(12) United States Patent
Linsley et al.

(10) Patent No.: US 6,271,002 B1
(45) Date of Patent: Aug. 7, 2001

(54) RNA AMPLIFICATION METHOD

(75) Inventors: Peter S. Linsley, Seattle; Janell M. Schelter, Bellevue, both of WA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/411,074

(22) Filed: Oct. 4, 1999

(51) Int. Cl.[7] .................................................. C12P 19/34
(52) U.S. Cl. ................................. 435/91.1; 435/4; 435/5; 435/6; 435/91.1; 435/91.2; 435/7.1; 435/288; 436/501; 536/24.3; 536/23.4
(58) Field of Search ..................... 435/91.1, 91.2, 435/6, 5, 4, 7.1, 288; 536/24.3, 23.4; 436/501

(56) References Cited

U.S. PATENT DOCUMENTS

| | | |
|---|---|---|
| 4,683,195 | 7/1987 | Mullis et al. |
| 4,683,202 | 7/1987 | Mullis . |
| 5,380,836 * | 1/1995 | Rogart ................................. 536/23.5 |
| 5,545,522 | 8/1996 | Van Gelder et al. |
| 5,716,785 | 2/1998 | Van Gelder et al. |
| 5,792,613 * | 8/1998 | Schmidt et al. .......................... 435/6 |
| 5,827,661 | 10/1998 | Blais . |
| 5,891,636 | 4/1999 | Van Gelder et al. |
| 5,965,352 * | 10/1999 | Stoughton et al. ....................... 435/4 |
| 6,040,138 | 3/2000 | Lockhart et al. |
| 6,046,165 * | 4/2000 | Laughon et al. ......................... 514/12 |
| 6,084,083 * | 7/2000 | Levinson ............................. 536/23.4 |

OTHER PUBLICATIONS

Lockhart et al., 1996, "Expression Monitoring by Hybridization to High–Density Oligonucleotide Arrays," *Nature Biotechnol.* 14:1675–80.

Gubler and Hoffman, 1983, "A simple and very efficient method for generating cDNA libraries," *Gene* 25(2–3):263–269.

Kwoh et al., 1989, "Transcription–based amplification system and detection of amplified human immunodeficiency virus type 1 with a bead–based sandwich hybridization format," *Proc Natl Acad Sci U S A* 86(4):1173–1177.

Murakawa et al., 1988, "Direct detection of HIV–1 RNA from AIDS and ARC patient samples," *DNA* 7(4):287–295.

Sarkar and Sommer, 1989, "Access to a messenger RNA sequence or its protein product is not limited by tissue or species specificity," *Science* 244(4902):331–334.

(List continued on next page.)

Primary Examiner—W. Gary Jones
Assistant Examiner—Janell E. Taylor
(74) Attorney, Agent, or Firm—Pennie & Edmonds LLP

(57) ABSTRACT

The present invention relates to methods and kits for amplification of mRNA using a primer in PCR that contains an RNA polymerase promoter. The invention provides methods for amplification and detection of RNA derived from a population of cells, preferably eukaryotic cells and most preferably mammalian cells, which methods preserve fidelity with respect to sequence and transcript representation, and additionally enable amplification of extremely small amounts of mRNA, such as might be obtained from $10^6$ mammalian cells. In typical embodiments of the invention, an RNA polymerase promoter (RNAP) is incorporated into ds cDNA by priming cDNA amplification by polymerase chain reaction (PCR) with an RNAP-containing primer. Following less than 20 cycles of PCR, the resultant RNAP-containing ds cDNA is transcribed into RNA using an RNA polymerase capable of binding to the RNAP introduced during cDNA synthesis. This combination of PCR and in vitro transcription (IVT) enables the generation of a relatively large amount of RNA from a small starting number of cells without loss of fidelity. RNAs generated using this method may be labeled and employed to profile gene expression in different populations of cells, e.g., by use of a polynucleotide microarray.

102 Claims, 5 Drawing Sheets

OTHER PUBLICATIONS

Figure 1:
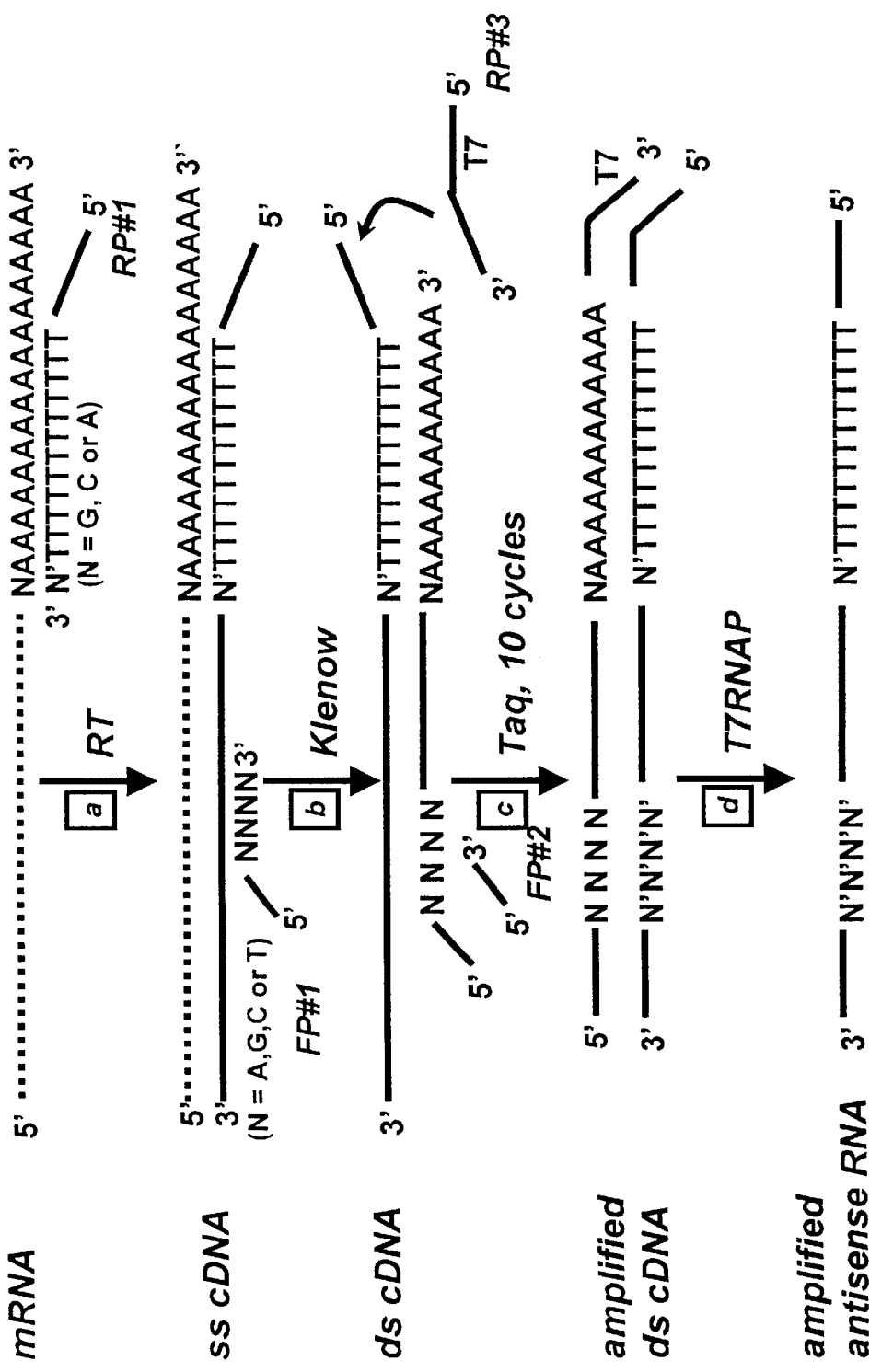

Sarkar et al., 1990, "Direct sequencing of the activation peptide and the catalytic domain of the factor IX gene in six species," *Genomics 6*(1):133–143.

Sarkar and Sommer, 1990, "The 'megaprimer' method of site–directed mutagenesis," *Biotechniques 8*(4):404–407.

Sommer et al., 1992, "PCR amplification of specific alleles (PASA) is a general method for rapidly detecting known single–base changes," *Biotechniques 12*(1):82–87.

Stoflet et al., 1988, "Genomic amplification with transcript sequencing," *Science 239*(4839):491–494.

Yang and Melera, 1992, "Application of the polymerase chain reaction to the ribonuclease protection assay," *Biotechniques 13*(6):922–927.

* cited by examiner

RNA AMPLIFICATION METHOD

1. INTRODUCTION

The present invention relates to oligonucleotide primers for amplification of nucleic acids that comprise a synthetic oligonucleotide containing an RNA promoter (an "RNAP-containing" primer). The present invention also relates to methods for amplification and detection of nucleic acids using RNAP-containing primers, and, more specifically, to methods for amplification and detection of RNA derived from a population of cells, preferably eukaryotic cells and most preferably mammalian cells, which methods preserve fidelity with respect to sequence and transcript representation, and additionally enable amplification of extremely small amounts of mRNA, such as might be obtained from $10^6$ mammalian cells. In typical embodiments of the invention, an RNA polymerase promoter (RNAP) is incorporated into ds cDNA by priming cDNA amplification by polymerase chain reaction (PCR) with an RNAP-containing primer. Following multiple cycles of PCR, the resultant RNAP-containing ds cDNA is transcribed into RNA using an RNA polymerase capable of binding to the RNAP introduced during cDNA synthesis. This combination of PCR and in vitro transcription (IVT) enables the generation of a relatively large amount of RNA from a small starting number of cells without loss of fidelity. RNAs generated using this method may be labeled and employed to profile gene expression in different populations of cells.

2. BACKGROUND OF THE INVENTION

Gene expression is important for understanding a wide range of biological phenomena, including development, differentiation, senescence, oncogenesis, and many other medically important processes. Recently, changes in gene expression have also been used to assess the activity of new drug candidates and to identify new targets for drug development. The latter objective is accomplished by correlating the expression of a gene or genes known to be affected by a particular drug with the expression profile of other genes of unknown function when exposed to that same drug; genes of unknown function that exhibit the same pattern of regulation, or signature, in response to the drug are likely to represent novel targets for pharmaceutical development.

Generally, the level of expression of the protein product of a gene and its messenger RNA (mRNA) transcript are correlated, so that measuring one provides you with reliable information about the other. Since in most instances it is technically easier to measure RNA than to measure protein, variations in mRNA levels are commonly employed to assess gene expression in different cells and tissues or in the same cells and tissues at different stages of disease or development or exposed to different stimuli. One particularly useful method of assaying gene expression at the level of transcription employs DNA microarrays (Ramsay, Nature Biotechnol. 16: 40–44, 1998; Marshall and Hodgson, Nature Biotechnol. 16: 27–31, 1998; Lashkari et al., Proc. Natl. Acad. Sci. (USA) 94: 130–157, 1997; DeRisi et al., Science 278: 680–6, 1997).

Mammalian cells contain as many as $1 \times 10^5$ to $3 \times 10^5$ different mRNA molecules, each of which varies in abundance (or frequency) within a given cell. The most abundant mRNAs are typically present at many thousands of copies per cell, while others may be present in as few as one copy or less per cell. Techniques for analyzing gene expression at the level of transcription typically require tens to hundreds of micrograms of mRNA, or as much as might be found in $10^7$-$10^9$ mammalian cells. Oftentimes, it is impractical to obtain this number of cells from a tissue of interest. For example, a blood sample typically contains $10^6$ nucleated cells/ml; hence, to obtain $10^9$ cells for analysis would necessitate taking a 1000 ml blood sample, which is clearly impractical in most instances.

Various methods have been described in the literature for amplifying the amount of a nucleic acid, such as deoxyribonucleic acid (DNA) and RNA, present in a sample. Among these, the most widely practiced is the polymerase chain reaction (PCR), described in U.S. Pat. No. 4,683,195 (Mullis et al., entitled "Process for amplifying, detecting, and/or-cloning nucleic acid sequences," issued Jul. 28, 1987) and U.S. Pat. No. 4,683,202 (Mullis, entitled "Process for amplifying nucleic acid sequences," issued Jul. 28, 1987), and herein incorporated by reference. Briefly, PCR consists of amplifying denatured, complementary strands of target nucleic acid by annealing each strand to a short oligonucleotide primer, wherein the primers are chosen so as to flank the sequence of interest. The primers are then extended by a polymerase enzyme to yield extension products that are themselves complementary to the primers and hence serve as templates for synthesis of additional copies of the target sequence. Each successive cycle of denaturation, primer annealing, and primer extension essentially doubles the amount of target synthesized in the previous cycle, resulting in exponential accumulation of the target.

When PCR is used to amplify mRNA into double-stranded (ds) DNA, the polyadenylated (poly(A)+) fraction is first selected, then a complementary DNA (cDNA) copy of the mRNA is made using reverse transcriptase and an oligo(dT) or random primer. The products of this reaction can be amplified directly using random priming (Ausubel et al., eds., 1994, Current Protocols in Molecular Biology, vol. 2, Current Protocols Publishing, New York).

PCR methodologies in general suffer from several limitations that are well-known in the art; see U.S. Pat. No. 5,716,785 (Van Gelder et al., entitled "Processes for genetic manipulations using promoters," issued Feb. 10, 1998) and Innis et al., eds. (1990, PCR Protocols: A Guide to Methods and Applications, Academic Press Inc., San Diego, Calif.) for review and discussion of limitations. One such limitation is due to the poor fidelity of commonly used, thermostable polymerase enzymes, such as Taq. This results in nucleotide base misincorporations that are propagated from one cycle to the next. It is estimated that such misincorporations may occur as often as once per one thousand bases of incorporation. A second limitation is that different cDNAs are amplified with different efficiencies, resulting in underrepresentation of some cDNA sequences and overrepresentation of others in the amplified product. Even a small difference in efficiency may result in a several-thousand fold differential in the representation of these cDNAs in the product after only 30 cycles of amplification.

An alternative method of mRNA amplification is known as in vitro transcription (IVT) and is described in U.S. Pat. No. 5,716,785 (Van Gelder et al., entitled "Processes for genetic manipulations using promoters," issued Feb. 10, 1998), which is herein incorporated by reference. Unlike PCR, IVT does not result in geometric amplification, but rather in linear amplification. In IVT, an oligo(dT) primer that is extended at the 5'-end with a bacteriophage T7 RNA polymerase promoter (RNAP) is used to prime the poly-A+ mRNA population for cDNA synthesis. After synthesis of the first-strand cDNA, the second-strand cDNA is made using the method of Gubler and Hoffman (Gene 25:263–69, 1983). Addition of RNA polymerase results in in vitro transcription and linear amplification of mRNA that is anti-sense to the poly-A+ RNA. While this method does not suffer from the same limitations in fidelity of amplification as PCR, it is also not as sensitive as PCR and requires a much larger sample of mRNA to generate the same amount of material as PCR. Because of its low efficiency, IVT is thus sometimes not a realistic alternative.

Two other types of nucleotide amplification are described in Stoflet et al. (Science 239:491–494, 1988) and in Sarkar & Sommer (Science 244: 331–334, 1989). Stoflet et al. (Science 239:491–494, 1988) describes a variation of PCR known as genomic amplification with transcript sequencing (GAWTS). In GAWTS, a phage promoter is attached to at least one of the two PCR primers. The DNA segments amplified by PCR are transcribed to further increase signal and to provide an abundance of single-stranded template for reverse transcriptase-mediated dideoxy sequencing. Sarkar & Sommer (Science 244: 331–334, 1989) describes a modification of the GAWTS method, known as RNA amplification with transcript sequencing (RAWTS). RAWTS consists of four steps: (i) cDNA synthesis with oligo(dT) or an mRNA-specific oligonucleotide primer, (ii) PCR where one or both oligonucleotides contains a phage promoter attached to a sequence complementary to the region to be amplified, (iii) transcription with a phage promoter, and (iv) reverse transcriptase-mediated dideoxy sequencing of the transcript, which is primed with a nested (internal) oligonucleotide. Both the GAWTS and RAWTS methods, however, involve relatively large numbers of PCR cycles, e.g. 27 rounds (Stoflet et al., Science 239:491–494, 1988) or 40 rounds (Sarkar & Sommer, Science 244: 331–334, 1989). As described above, large numbers of PCR cycles have at least two serious drawbacks: (1) propagation of misincorporations from one cycle to the next, increasing the inaccuracy of the amplification, and (2) different efficiencies of amplification, resulting in underrepresentation or overrepresentation of some cDNA sequences in the amplified product.

There exists a need in the art for improved methods of amplifying nucleic acids, especially mRNA, which methods can achieve a high degree of amplification from a limited amount of mRNA and which simultaneously avoid the infidelity with respect to sequence and representation often introduced by other amplification methods. The present invention is believed to satisfy this need and to provide other related advantages.

Citation of a reference herein shall not be construed as an admission that such reference is prior art to the present invention.

3. SUMMARY OF THE INVENTION

The present invention relates to oligonucleotide primers for amplification of nucleic acids that comprise a synthetic oligonucleotide containing an RNA promoter (an "RNAP-containing" primer). The present invention also relates to methods for amplification and detection of nucleic acids using RNAP-containing primers, and, more specifically, to methods for amplification and detection of RNA derived from a population of cells, preferably eukaryotic cells and most preferably mammalian cells, which methods preserve fidelity with respect to sequence and transcript representation, and additionally enable amplification of extremely small amounts of mRNA, such as might be obtained from $10^6$ mammalian cells. In typical embodiments of the invention, an RNA polymerase promoter (RNAP) is incorporated into ds cDNA by priming cDNA amplification by polymerase chain reaction (PCR) with an RNAP-containing primer. Following multiple cycles of PCR, the resultant RNAP-containing ds cDNA is transcribed into RNA using an RNA polymerase capable of binding to the RNAP introduced during cDNA synthesis. This combination of PCR and in vitro transcription (IVT) enables the generation of a relatively large amount of RNA from a small starting number of cells without loss of fidelity. RNAs generated using this method may be labeled and employed to profile gene expression in different populations of cells.

In one embodiment, the invention is directed to a method for amplifying at least one mRNA in a sample containing a plurality of different mRNAs comprising (a) synthesizing first strand cDNA by contacting under conditions conducive to reverse transcriptase activity at least one mRNA in said sample with (i) reverse transcriptase, and (ii) a first primer that is sufficiently complementary to a sequence in the mRNA so as to prime synthesis in a direction toward the 5' end of the mRNA; (b) synthesizing double-stranded cDNA by contacting under conditions conducive to DNA polymerase activity the first strand cDNA with (i) a first DNA polymerase, and (ii) a second primer that is sufficiently complementary to a sequence 5' to said first primer sequence in said first strand cDNA so as to prime synthesis in a direction toward said first primer sequence; wherein neither said first primer nor said second primer comprises an RNA polymerase promoter sequence in sense or antisense orientation; (c) amplifying the double-stranded cDNA by subjecting the double-stranded cDNA to a single round of polymerase chain reaction (hereinafter "PCR") of 20 cycles or less, wherein DNA is synthesized by use of a second DNA polymerase and a primer pair comprising a forward primer and a reverse primer, said forward primer and said reverse primer each being sufficiently complementary to a different strand of said double-stranded cDNA so as to prime synthesis in a template-dependent manner, wherein said forward primer or reverse primer comprises an RNA polymerase promoter sequence in sense or antisense orientation; and (d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced.

In another embodiment, the invention is directed to the above amplifying method, further comprising, after the transcribing step, determining the presence or absence of a preselected target mRNA in said sample.

In a specific embodiment, the invention is directed to an amplifying method, wherein the mRNA is extracted from at least one cell of interest, and further comprising contacting the cRNA produced with an array containing one or more species of polynucleotide positioned at preselected sites on the array, under conditions conducive to hybridization; and detecting any hybridization that occurs between the one or more species of polynucleotide and the cRNA.

In another embodiment, the invention is directed to a method for comparing the presence or amount of at least one mRNA of interest in a first sample and in a second sample, said first sample and said second sample each containing a plurality of different mRNAs from one or more cells, comprising: (a) synthesizing first strand cDNA by contacting under conditions conducive to reverse transcriptase activity at least one mRNA in said first sample with (i) reverse transcriptase, and (ii) a first primer that is sufficiently complementary to a sequence in the mRNA so as to prime synthesis in a direction toward the 5' end of the mRNA; (b) synthesizing double-stranded cDNA by contacting under conditions conducive to DNA polymerase activity the first strand cDNA with (i) a first DNA polymerase, and (ii) a second primer that is sufficiently complementary to a sequence 5' to said first primer sequence in said first strand cDNA so as to prime synthesis in a direction toward said first primer sequence; wherein neither said first primer nor said second primer comprises an RNA polymerase promoter sequence in sense or antisense orientation; (c) amplifying the double-stranded cDNA by subjecting the double-stranded cDNA to a single round of PCR of 20 cycles or less, wherein DNA is synthesized by use of a second DNA polymerase and a primer pair comprising a forward primer and a reverse primer, said forward primer and said reverse primer each being sufficiently complementary to a different strand of said double-stranded cDNA so as to prime synthesis in a template-dependent manner, wherein said forward primer or reverse primer comprises an RNA polymerase promoter sequence in sense or antisense orientation; (d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced; (e) labeling the cRNA produced in step (d) with a first label; (f) repeating steps (a)–(d) with said second sample; (g) labeling the cRNA produced in step (f) with a second label distinguishable from said first label; (h) detecting or measuring the mRNA of interest in the first sample by contacting the cRNA labeled with said first label with a polynucleotide probe capable of hybridizing to said cRNA of the mRNA of interest under conditions conducive to hybridization; and detecting any hybridization that occurs between said probe and said cRNA; (i) detecting or measuring the mRNA of interest in the second sample by contacting the cRNA labeled with said second label with said polynucleotide probe capable of hybridizing to said cRNA of the mRNA of interest under conditions conducive to hybridization; and detecting any hybridization that occurs between said probe and said cRNA; and (j) comparing the mRNA of interest detected or measured in said first sample with the mRNA of interest detected or measured in said second sample.

In a specific embodiment of the above method, in steps (h) and (i), the steps of contacting the cRNA labeled with said first label with said polynucleotide probe, and contacting the cRNA labeled with said second label with said polynucleotide probe, are carried out concurrently.

In another specific embodiment of the method described above, the first sample contains mRNAs from cells that are diseased, and the second sample contains mRNAs from cells that are not so diseased.

In another embodiment, the invention is directed to a kit comprising in one or more containers (a) a mixture of first primers, each first primer comprising an oligo (dT) sequence and a 3' end sequence of 1–5 nucleotides, and said mixture of first primers comprising primers having A, G, and C, respectively, present in each position of said 3' end sequence, wherein each primer in said mixture of first primers further comprises at its 5' end an identical selected sequence of 5–12 nucleotides; (b) a mixture of second primers, each second primer comprising at its 5' end an identical selected sequence of 8–12 nucleotides, and at its 3' end a sequence of 1–6 nucleotides, said mixture of second primers comprising primers having A, G, C and T, respectively, present in each position of said 3' end sequence; and (c) a primer pair suitable for use in PCR, said primer pair comprising a forward primer and a reverse primer, wherein said forward primer or reverse primer comprises an RNA polymerase promoter sequence in sense or antisense orientation.

The method of this invention involves the incorporation of an RNA polymerase promoter (RNAP) into ds cDNA by priming cDNA amplification by PCR with a primer comprising a synthetic oligonucleotide containing the promoter sequence in sense or antisense orientation ("RNAP-containing primer"). Following PCR of no more than 20, 15, or 10 cycles, the resultant RNAP-containing double-stranded (ds) cDNA is transcribed into RNA using an RNA polymerase capable of binding to the RNAP introduced during cDNA synthesis. This combination of PCR and in vitro transcription (IVT) enables the generation of a relatively large amount of RNA from a small starting number of cells without loss of fidelity.

In another embodiment of the invention, a label or labels may be introduced into the RNA during the transcription step to facilitate gene expression profiling in different populations of cells.

Kits for carrying out the amplification methods of the invention are also provided.

3.1. DEFINITIONS

As used herein, the following terms shall have the abbreviations indicated.

ASP, allele-specific polymerase chain reaction

FP, forward primer

IVT, in vitro transcription mAb, monoclonal antibody

ORF, open reading frame

PHA, phytohemagglutinin

RNAP, RNA polymerase

RP, reverse primer

T7RNAP, T7 RNA polymerase promoter

4. DESCRIPTION OF THE FIGURES

FIG. 1. Schematic representation of a 3'-end PCR/IVT method of the invention. (a) RNA obtained from a population of cells is reverse transcribed into single-stranded (ss) cDNA using reverse primer RP#1 (SEQ ID NO:1), which hybridizes to the 3' end of the mRNA. (b) The resulting first-strand, antisense cDNA is then converted into double-stranded (ds) cDNA using the Klenow fragment of DNA polymerase I and forward primer FP#1, (SEQ ID NO:4) which hybridizes to the 3' end of the first-strand, antisense cDNA. (c) ds cDNA is then amplified by PCR using Taq polymerase. Ten cycles of PCR are performed, using forward primer FP#2 (SEQ ID NO:5) and reverse primer RP#3 (SEQ ID NO:3). FP#2 hybridizes to the 3' end of the first-strand, antisense cDNA. RP#3 hybridizes to the 3' end of the second-strand, sense cDNA and contains an RNA polymerase promoter sequence. The reverse primer hybridizes to a region of the ds DNA that is downstream from the region to which the forward primer hybridizes. The arrow indicates that the sequence of RP#3 is antisense and corresponds to the 5' end of the first-strand, antisense cDNA. (d) Amplified, ds cDNA is transcribed into antisense RNA using T7RNAP, resulting in the amplification of antisense RNA.

Figure 2:
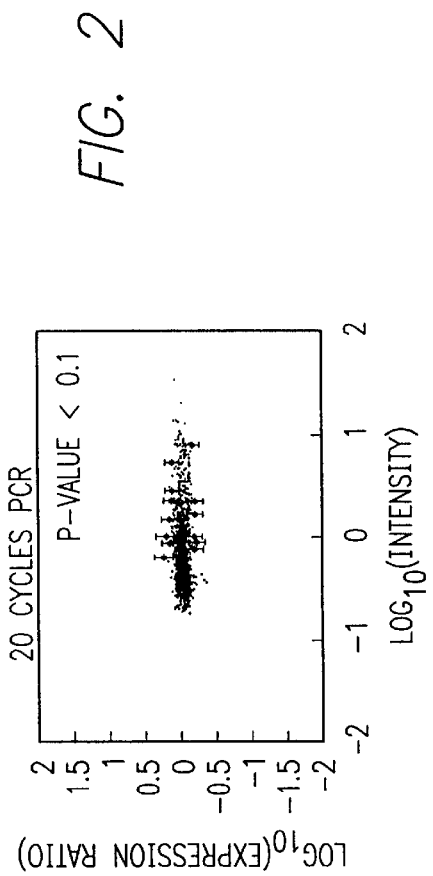
Figure 2:
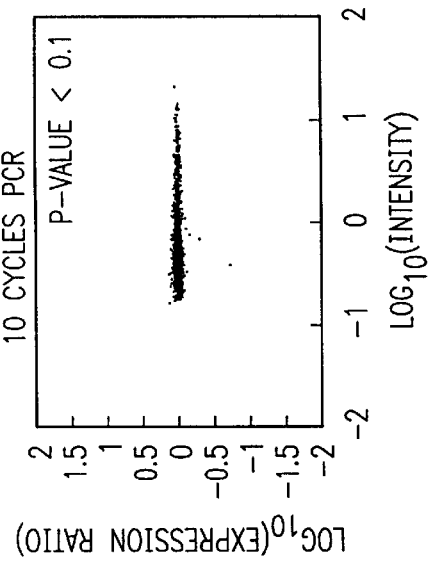
Figure 2:
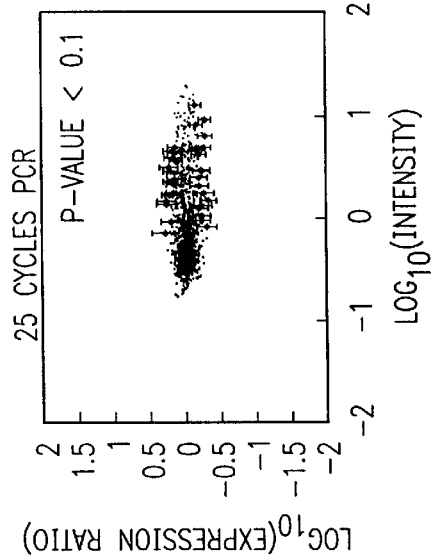
Figure 2:
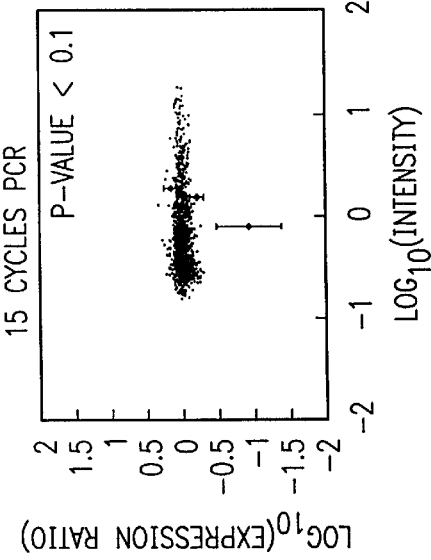

FIG. 2. Comparison of the effect of different numbers of cycles of PCR amplification on the representation of mRNA sequences from *Saccharomyces cerevisiae*. mRNA was prepared from wild type (wt) yeast *Saccharomyces cerevisiae* by the method of Zhao et al. (*BioTechniques* 24: 842–50, 852, 1998). The number of cycles of PCR performed varied between 10 and 25. For each cycle number, two 3' cDNA pools were prepared in parallel and labeled with different fluorophores (one red (Cy5), the other green (Cy3)). Yeast half-genome arrays were then probed in duplicate with each of the cDNA pools prepared as described in Section 6 (Example 1) below. Microarrays were imaged as described in Section 6 and expression profiles were generated for each cycle number. Expression ratios were calculated as the ratio of Cy 5:Cy 3 hybridization ("red:green ratio").

The data indicate that when 15–25 cycles of PCR were performed (panels A–C), a large number of ORFs exhibited expression ratios that deviated from unity. In panels A–C, the dark grey error bars that appear above the "cloud" of data points indicate deviations from unity of expression ratios, i.e., of ORFs preferentially hybridized with the Cy 5 labeled sample. The light grey error bars that appear below the "cloud" of data points indicate deviations from unity of expression ratios i.e., of ORFs preferentially hybridized with the Cy 3 labeled sample. However, when only 10 cycles of PCR were performed (panel D), there was essentially no deviation from unity for any ORF profiled, indicating that no bias was introduced.

Figure 3:
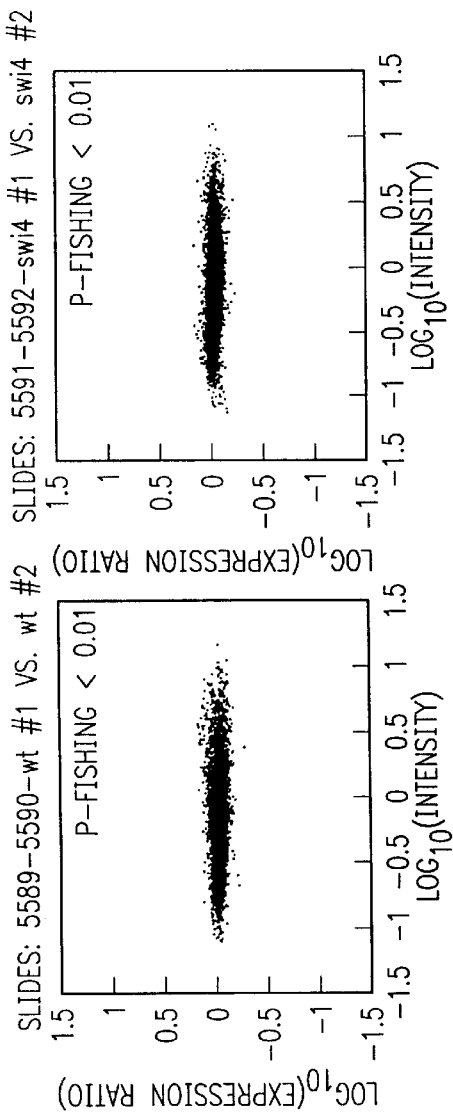
Figure 3:
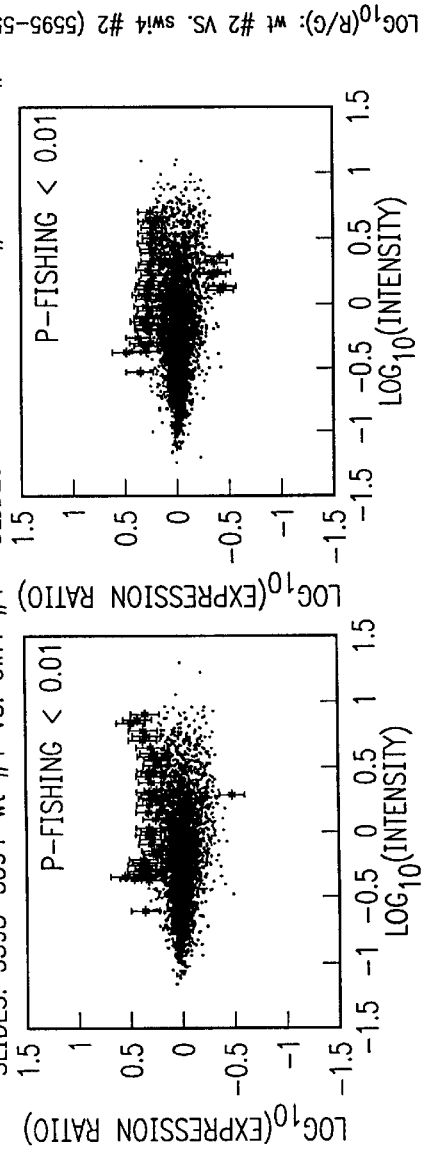

FIG. 3. 3'-end PCR/IVT procedure gives reproducible signatures. RNA from wild type yeast and from a mutant yeast strain designated swi4 was amplified and labeled with one of two different fluorophores, either Cy 3 or Cy 5, using the 3'-end PCR/IVT method of the invention, as described in Section 7 (Example 2). Labeled cRNAs were then used to probe yeast full genome arrays in various pairwise combinations as described in Section 7, the arrays were imaged as described in Section 6, and expression profiles were generated for each pairwise combination. In panels A and B, where like strains were compared to like strains, there was no statistically significant deviation from unity at the p<0.01 level. On the other hand, in panels C and D, where like was compared to unlike, the $\log_{10}$(expression ratio) deviated significantly from unity, reflecting the differences in gene expression between the two yeast strains. Panel E shows a correlation plot comparing the values displayed in panel C versus the values in panel D. Panel E shows that the swi4 samples shown in panels C and D are amplified equivalently.

Figure 4:
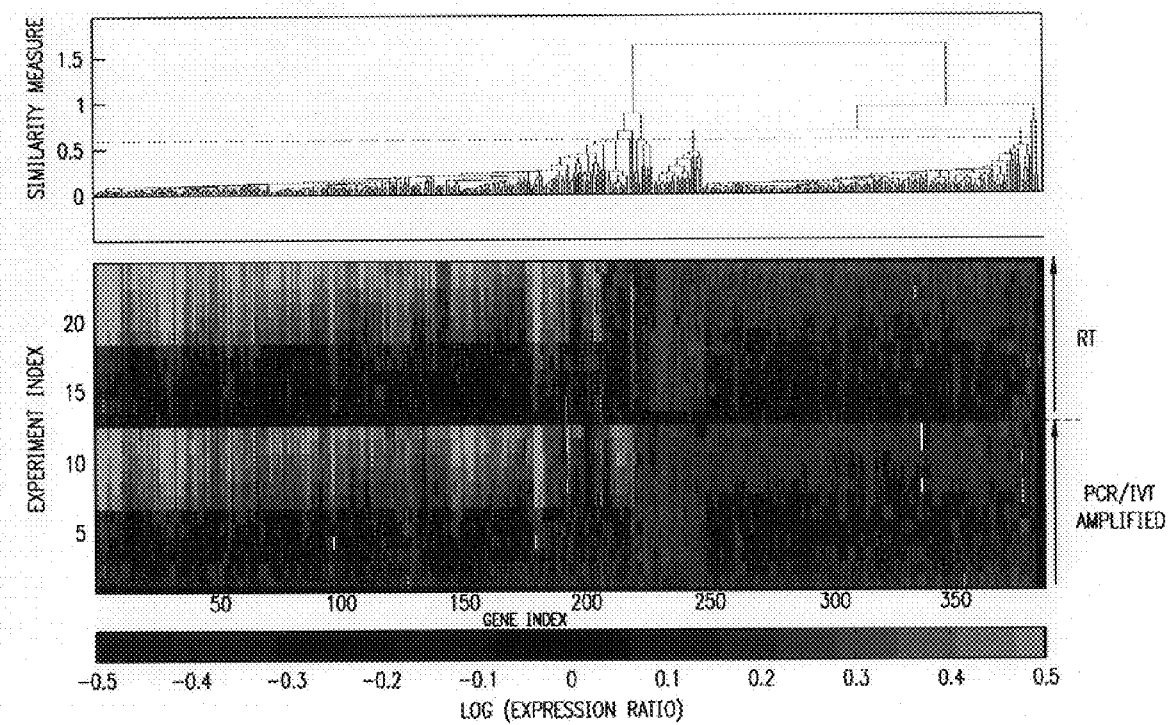

FIG. 4. Similarity between gene regulation profiles detected with antisense RNA amplified by the PCR/IVT method and with cDNA prepared by conventional reverse transcriptase methods. For experimental details, see Section 8. Amplified and labeled RNA or labeled cDNA molecules from drug-treated cells were mixed with labeled samples from untreated cells and these were then simultaneously hybridized to full genome S. cerevisiae DNA microarrays. RNA was amplified and labeled using the PCR/IVT method of this invention. cDNA was labeled according to Marton et al. (Nature Med. 4: 1293–1301, 1998).

A set of 385 genes that were significantly up- or down-regulated (p<0.01) following drug treatment, as detected by either method, were then grouped according to their co-regulation behavior across this set of experiments. Grouping was done using the 'hclust' hierarchical clustering algorithm as implemented in Matlab (MathWorks, Natick, Mass.). The distance metric for any gene pair is assigned typically to be 1−r, where r is the correlation coefficient of the regulation behavior of one gene compared with the other gene. The hierarchical clustering data is displayed in the top plot (entitled "Similarity Measure"). The left-hand branch and cluster of the two hierarchical clusters depicted depicts up-regulated genes. The right-hand branch and cluster depicts down-regulated genes.

The original up- and down-regulations for the chosen genes were then displayed in a color tabular format, a black-and-white copy of which is reproduced in the middle plot entitled "Experiment Index". Green (here depicted on the left-hand portion of the Experiment Index as lighter gray) denotes up regulation, and red (here depicted on the right-hand portion of the Experiment Index as darker grey) denotes down regulation. The gene order follows the order in the hierarchical clustering tree. Arrows indicate increasing concentrations of FK506. The profiles show that the amplification procedure allows >~2,000-fold amplification while introducing minimal biases.

Figure 5:
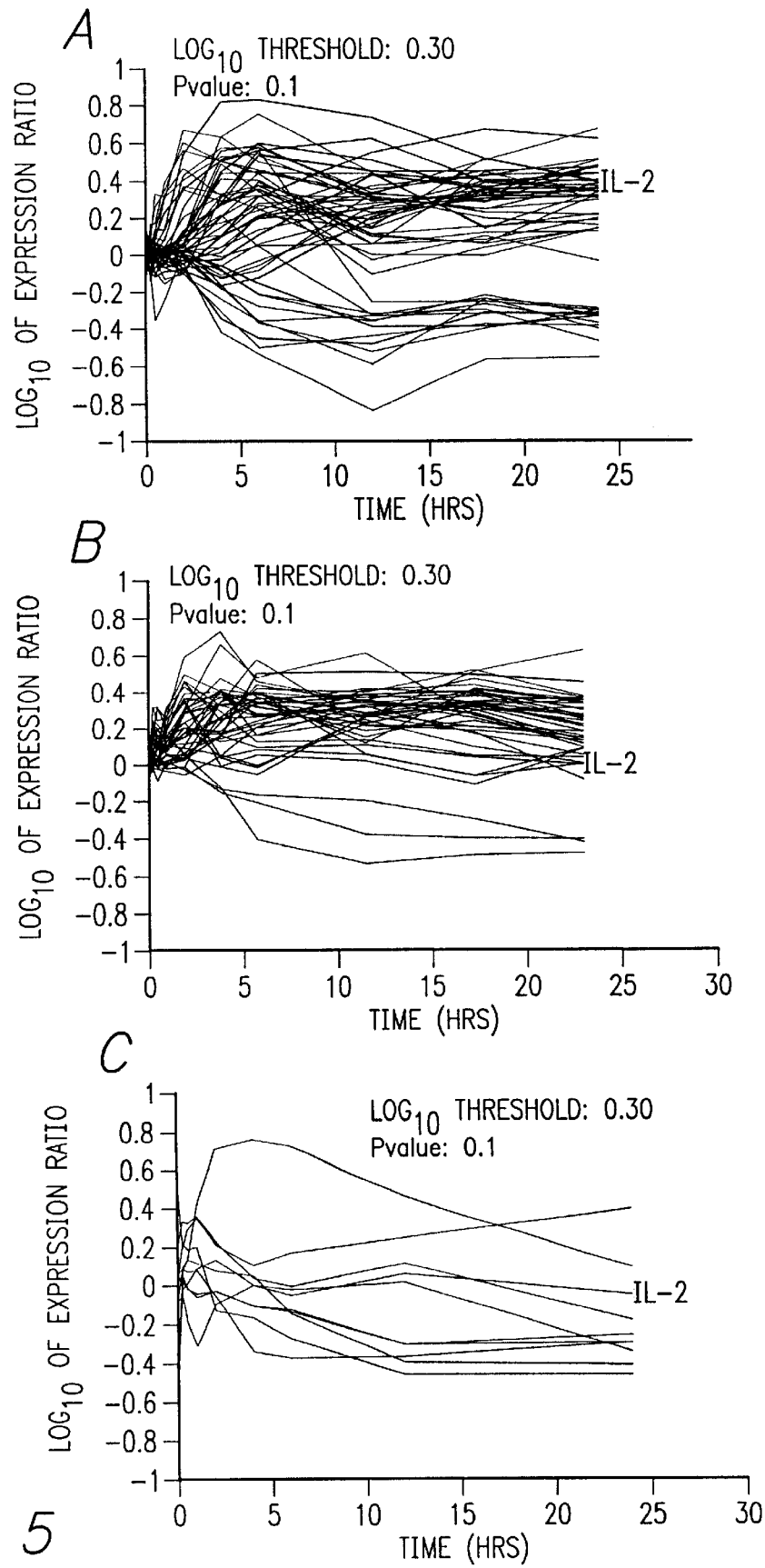

FIG. 5. Kinetic analysis of transcript regulation during T cell activation. For experimental details, see Section 9. Mononuclear cells from 60 ml of human peripheral blood were cultured for 5 days with the phytohemagglutinin (PHA), then rested for one day. Individual cultures were then incubated for 3 hrs with no drug (untreated) (FIG. 5a), with the drug FK506 (10 ng/ml) (FIG. 5b), or with PP2 (tyrosine kinase inhibitor, 12 mg/ml) (FIG. 5c). Cells were then activated with anti-CD3 monoclonal antibody (mAb) and anti-CD28mAb. At the indicated times, cultures were harvested and total cellular RNA was isolated and amplified by PCR/IVT. Labeled RNA pools representing unactivated cells amplified from ~1.5 ml of blood were mixed with RNA pools from the same number of cells activated minus or plus the indicated drugs, and hybridized to a DNA microarray comprising ~2,000 distinct human cDNAs. Identical samples were harvested at the indicated times following initiation of activation.

The $\log_{10}$ ratios of gene expression are shown in activated cells versus unactivated cells for genes that were up or down regulated at a significance of p<0.1 by at least two-fold ($\log_{10}>0.3$) in samples collected from at least two time points. Up regulated genes have $\log_{10}$ expression ratios >0, and down regulated genes have $\log_{10}$ expression ratios <0. Fewer genes are displayed in the drug-treated samples because these drugs blocked gene expression of characteristic genes. For reference, the kinetic behavior of IL-2 transcript is plotted in each panel.

5. DETAILED DESCRIPTION OF THE INVENTION

The present invention relates to oligonucleotide primers for amplification of nucleic acids that comprise a synthetic oligonucleotide containing an RNA polymerase promoter (RNAP) The invention further relates to methods of use of the oligonucleotide primers of the invention for amplification of nucleic acids.

The present invention provides methods for the amplification of nucleic acid sequences in a population of cells, which methods preserve fidelity with respect to sequence and transcript representation, and additionally enable amplification of extremely small amounts of mRNA, such as might be obtained from $10^6$ mammalian cells. Sequence fidelity shall be considered to have been maintained if the mean rate of misincorporation of bases in the final product using the methods of this invention is preferably less than or equal to 1 per 250 bases incorporated, more preferably less than or equal to 1 per 500 bases incorporated, and most preferably less than or equal to 1 per 1000 bases incorporated. In the present invention, representational fidelity is considered to have been maintained if the $\log_{10}$ (expression ratio) for any given sequence amplified by the methods of the invention is preferably less than or equal to 0.1 or −0.1., more preferably less than or equal to 0.3 or −0.3, and most preferably, less than or equal to 0.5 or −0.5.

For clarity of disclosure, and not by way of limitation, the detailed description of the invention is divided into the subsections set forth below.

5.1. OLIGONUCLEOTIDES

The oligonucleotide primers for use in the methods of the invention can be of any suitable size, and are preferably 24–48 nucleotides in length.

The oligonucleotide primers can be DNA, RNA, chimeric mixtures or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming the desired amplification reaction.

For example, the oligonucleotide primer may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide primer comprises at least one modified sugar moiety selected from the group including but not limited to arabinose, 2-fluoroarabinose, xylulose, and hexose.

In yet another embodiment, the oligonucleotide primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide primers of the present invention may be derived by cleavage of a larger nucleic acid fragment using non-specific nucleic acid cleaving chemicals or enzymes or site-specific restriction endonucleases; or by synthesis by standard methods known in the art, e.g. by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (1988, Nucl. Acids Res. 16:3209–3221), methylphosphonate oligonucleotides can be prepared by use of controlled pore glass polymer supports (Sarin et al., 1988, Proc. Natl. Acad. Sci. U.S.A. 85:7448–7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

5.2. METHODS OF LABELING OF NUCLEIC ACID AMPLIFICATION PRODUCTS

Nucleic acid amplification products such as amplified RNA may be labeled with any art-known detectable marker, including radioactive labels such as $^{32}P$, $^{35}S$, $^{3}H$, and the like; fluorophores; chemiluminescers; or enzymatic markers. In a preferred embodiment, the label is fluorescent. Exemplary suitable fluorophore moieties that can be selected as labels are set forth in Table 1.

Table 1. Suitable fluorophore moieties that can be selected as labels 4-acetamido-4'-isothiocyanatostilbene-2,2'disulfonic acid
acridine and derivatives:
   acridine
   acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)
-(4-anilino-1-naphthyl)maleimide
anthranilamide
Brilliant Yellow
coumarin and derivatives:
   coumarin
   7-amino-4-methylcoumarin (AMC, Coumarin 120)
   7-amino-4-trifluoromethylcoumarin (Coumarin 151)
Cy3
Cy5
cyanosine
4',6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:
   eosin
   eosin isothiocyanate
erythrosin and derivatives:
   erythrosin B
   erythrosin isothiocyanate
ethidium
fluorescein and derivatives:
   5-carboxyfluorescein (FAM)
   5-(4,6-dichlorotriazin-2-yl)aminofluorescein (DTAF)
   2'7'-dimethoxy-4'5'-dichloro-6-carboxyfluorescein (JOE)
   fluorescein
   fluorescein isothiocyanate
   QFITC (XRITC)
fluorescamine
IR144
IR1446
Malachite Green isothiocyanate
4-methylumbelliferone
ortho cresolphthalein
nitrotyrosine
pararosaniline Phenol Red
B-phycoerythrin
o-phthaldialdehyde
pyrene and derivatives:
   pyrene
   pyrene butyrate
   succinimidyl 1-pyrene butyrate
Reactive Red 4 (Cibacron® Brilliant Red 3B-A)
rhodamine and derivatives:
   6-carboxy-X-rhodamine (ROX)
   6-carboxyrhodamine (R6G)
   lissamine rhodamine B sulfonyl chloride
   rhodamine (Rhod)
   rhodamine B
   rhodamine 110
   rhodamine 123
   rhodamine X isothiocyanate
   sulforhodamine B
   sulforhodamine 101
   sulfonyl chloride derivative of sulforhodamine 101 (Texas Red)
   N,N,N'N'-tetramethyl-6-carboxyrhodamine (TAMRA)
   tetramethyl rhodamine
   tetramethyl rhodamine isothiocyanate (TRITC)
riboflavin
rosolic acid
terbium chelate derivatives The preferred label in the methods of this invention is a fluorophore, such as fluorescein isothiocyanate, lissamine, Cy3, Cy5, and rhodamine 110, with Cy3 and Cy5 particularly preferred.

Not only fluorophores, but also chemiluminescers and enzymes, among others, may be used as labels. In another embodiment, the oligonucleotide may be labeled with an enzymatic marker that produces a detectable signal when a particular chemical reaction is conducted, such as alkaline phosphatase or horseradish peroxidase. Such enzymatic markers are preferably heat stable, so as to survive the denaturing steps of the amplification process.

Oligonucleotides may also be indirectly labeled by incorporating a nucleotide linked covalently to a hapten or to a molecule such as biotin, to which a labeled avidin molecule or streptavidin may be bound, or digoxygenin, to which a labeled anti-digoxygenin antibody may be bound.

Oligonucleotides of the invention may be labeled with labeling moieties during chemical synthesis or the label may be attached after synthesis by methods known in the art.

5.2.1. LABELING OF RNA

In one embodiment, the amplified RNA of the invention is labeled during amplification to facilitate its detection in subsequent steps. The RNA may be labeled with any art-known detectable marker, including but not limited to radioactive labels such as $^{32}P$, $^{35}S$, $^{3}H$, and the like; fluorophores; chemiluminescers; or enzymatic markers.

Labeling of RNA is preferably accomplished by including one or more labeled NTPs in the IVT reaction mixture. NTPs may be directly labeled with a radioisotope, such as $^{32}P$, $^{35}S$, $^{3}H$; radiolabeled NTPs are available from several sources, including New England Nuclear (Boston, Mass.) and Amersham. NTPs may be directly labeled with a fluorescent label such as Cy3 or Cy5. In one embodiment, biotinylated or allylamine-derivatized NTPs are incorporated during the IVT reaction and the resultant cRNAs thereafter labeled indirectly, for example, by the addition of fluorophore-conjugated avidin, in the case of biotin, or the NHS ester of a fluorophore, in the case of allylamine. In another embodiment, fluorescently labeled NTPs may be incorporated during the IVT reaction, which fluorescently labels the resultant cRNAs directly.

Exemplary fluorophore moieties that can be used as labels are set forth in Table 1 above. The preferred label in the methods of this invention is a fluorophore, such as fluorescein isothiocyanate, lissamine, Cy3, Cy5, and rhodamine 110, with Cy3 and Cy5 particularly preferred.

Not only fluorophores, but also chemiluminescers and enzymes, among others, may be used as labels. In yet another embodiment, the RNA may be labeled with an enzymatic marker that produces a detectable signal when a particular chemical reaction is conducted, such as alkaline phosphatase or horseradish peroxidase. Such enzymatic markers are preferably heat stable, so as to survive the denaturing steps of the amplification process.

RNA may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. RNA may be labeled with labeling moieties during chemical synthesis or the label may be attached after synthesis by methods known in the art.

Labeling of RNA is preferably accomplished by preparing cRNA that is fluorescently labeled with NHS-esters. Most preferably, labeling of RNA is accomplished in a two-step procedure in which allylamine-derivatized UTP is incorporated during IVT. Following the IVT reaction, unincorporated nucleotides are removed and the allylamine-containing RNAs are conjugated to the N-hydroxysuccinimide (NHS) esters of Cy3 or Cy5.

This two-step method of preparing fluorescent-labeled cRNA is relatively inexpensive and suitable for use in two color hybridizations to DNA microarrays. In the first step, aminoallyl (AA)-labeled nucleic acids are prepared by incorporation of AA-nucleotides. AA-UTP (Sigma A-5660) may be used for labeling cRNA. AA-cRNA is prepared using the Ambion MegaScript T7 RNA polymerase in vitro transcription kit, with AA-UTP substituted at 50–100% of the total UTP concentration. It is essential to remove all traces of amine-containing buffers such as Tris prior to derivatizing the AA-nucleic acids. AA-nucleic acids prepared in enzymatic reactions are preferably cleaned up on appropriate QIAGEN columns: RNeasy® Mini kit (for RNA) or QIAquick PCR Purification kit (for DNA) (QIAGEN Inc.—USA, Valencia, Calif.). For the QIAGEN columns, samples are applied twice. For washes, 80% EtOH is preferably substituted for the buffer provided with the QIAGEN kit. Samples are eluted twice with 50 µl volumes of 70° C. $H_2O$. Alternatively (but less preferably), samples may be cleaned up by repeated cycles of dilution and concentration on Microcon-30 filters.

In the second step, AA-nucleic acids are derivatized with NHS-esters, preferably Cy 3 or Cy 5. Preferably, 2–6 µg of AA-labeled nucleic acid are aliquoted into a microfuge tube, adjusting the total volume to 12 µl with $H_2O$. The NHS-ester is dissolved at a concentration of ~15 mM in anhydrous DMSO (~200 nmoles in 13 µl). 27 µl of 0.1 M sodium carbonate buffer, pH 9, are added. 12 µl of the dye mix (containing ~60 nmoles dye-NHS ester) are then immediately added to the AA-labeled nucleic acid (~6–20 pmoles of a 1 kb molecule). The samples are then incubated in the dark at 23° C. for 1 hour. The coupling reaction is stopped by adding 5 µl of a 4M solution of hydroxylamine. Incubation is continued at 23° C. for an additional 0.25 hr. Dye-coupled nucleic acid is separated from unincorporated dye on an RNeasy® Mini kit or QIAquick PCR Purification kit (QIAGEN Inc.—USA, Valencia, Calif.). Samples are washed with 80% EtOH instead of buffer, as described above, and eluted twice with 50 µl volumes of 70° C. H$_2$O.

The spectrum of the labeled nucleic acid is preferably measured from 220 nm–700 nm. The percent recovery of nucleic acid and molar incorporation of dye is calculated from extinction coefficients and absorbance values at $1_{max}$. Recovery of nucleic acid is typically ~80%. The mole percent of dye incorporated per nucleotide ranges from 1.5–5% of total nucleotides.

Often it is desired to compare gene expression in two different populations of cells, perhaps derived from different tissues or perhaps exposed to different stimuli. Such comparisons are facilitated by labeling the RNAs from one population with a first fluorophore and the RNAs from the other population, with a second fluorophore, where the two fluorophores have distinct emission spectra. Again, Cy3 and Cy5 are particularly preferred fluorophores for use in comparing gene expression between two different populations of cells.

5.3. METHODS OF PREPARATION OF RNA

The methods of the invention are applicable to nucleic acid sequences derived from both eukaryotic and prokaryotic cells, although they are preferably used with eukaryotic cells, and most preferably, with mammalian cells. Among cells that may serve as sources of DNA or RNA are nucleated blood cells, established cell lines, tumor cells, and tissue biopsy specimens, among others that will be readily apparent to those of skill in the art.

Although the amplification methods of the invention can be adapted to amplify DNA, it is preferred to utilize the methods to amplify RNA from a population of cells. Total cellular RNA, cytoplasmic RNA, or poly(A)+ RNA may be used. Methods for preparing total and poly(A)+ RNA are well known and are described generally in Sambrook et al. (1989, *Molecular Cloning—A Laboratory Manual* (2nd Ed.), Vols. 1–3, Cold Spring Harbor Laboratory, Cold Spring Harbor, N.Y.) and Ausubel et al., eds. (1994, *Current Protocols in Molecular Biology,* vol. 2, Current Protocols Publishing, New York).

RNA may be isolated from eukaryotic cells by procedures that involve lysis of the cells and denaturation of the proteins contained therein. Cells of interest include wild-type cells, drug-exposed wild-type cells, modified cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., 1979, Biochemistry 18:5294–5299). Poly(A)+ RNA is selected by selection with oligo-dT cellulose (see Sambrook et al., 1989, *Molecular Cloning—A Laboratory Manual* (2nd Ed.), Vols. 1–3, Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., eds., 1994, *Current Protocols in Molecular Biology,* vol. 2, Current Protocols Publishing, New York). Once bound, poly(A)+ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise at least 500, 1,000, 5,000, 10,000, 20,000, 30,000, 40,000, 50,000, 60,000, 70,000, 80,000 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences.

In a specific embodiment, total RNA or mRNA from cells are used in the methods of the invention. The source of the RNA can be cells of a plant or animal, human, mammal, primate, non-human animal, dog, cat, mouse, rat, bird, yeast, eukaryote, prokaryote, etc. In specific embodiments, the method of the invention is used with a sample containing total mRNA or total RNA from $1\times10^6$ cells or less.

5.4. METHODS OF DOUBLE-STRANDED cDNA SYNTHESIS

Double-stranded cDNA molecules can be synthesized from a collection of mRNAs present in a population of cells by methods well-known in the art. In order for the resultant ds cDNAs to be useful in the methods of this invention, it is necessary to incorporate an RNAP into these molecules during PCR amplification so that they can serve as templates for RNA transcription.

In the method of this invention, the first-strand cDNA is preferably produced by reverse transcription, wherein DNA is made from RNA using the enzyme reverse transcriptase. Reverse transcriptase is found in all retroviruses and is commonly obtained from avian myeloblastoma virus or Moloney murine leukemia virus; enzyme from these sources is commercially available from Life Technologies (Gaithersburg, Md.) and Boehringer Mannheim (Indianapolis, Ind.).

In general, it is preferred to use the poly(A) tail of mRNA for reverse transcription, using an oligo(dT)-containing primer. When oligo(dT) priming is employed, the primer will preferably contain about 12–15 T nucleotides, most preferably 14 T nucleotides. In a specific embodiment, the primer for reverse transcription contains between 5–50 T nucleotides. In a specific embodiment, the reverse transcription reaction is primed using random (degenerate) primers, e.g., that will prime first strand cDNA synthesis for substantially all the mRNAs in the sample. Preferably, the primer is a mixture of primers that contain oligo dT as their 5' sequence, and further comprise 1–5 degenerate bases as an anchor at their 3' end, more preferably 1–3 degenerate bases, and most preferably 1 degenerate base downstream of the oligo (dT); the degenerate base may be A, G, or C. In an embodiment wherein the RNA-containing sample contains purified polyA$^+$ RNA (mRNA), the first strand cDNA synthesis primer can (but need not be) totally random, e.g., a mixture of random hexamers of sequence N$_6$, wherein N=A, G, C or T (alternatively, an oligo dT-containing primer can be used). In an embodiment wherein the RNA-containing sample contains total RNA, preferably a primer comprising an oligo (dT) sequence is used for first strand cDNA synthesis; a totally random primer is preferably not used so as to avoid use of ribosomal RNA as template.

In a preferred embodiment, the primer for first strand cDNA synthesis is a mixture of primers that prime synthesis in a direction toward the 5' end of substantially all the mRNAs in the sample, and the primer for second strand cDNA synthesis is a mixture of primers that prime synthesis of double-stranded cDNA from substantially all the first strand cDNAs thus produced.

Thus, in a specific embodiment, the primer for first strand cDNA synthesis is a mixture of primers, each primer comprising an oligo (dT) sequence and a 3' end sequence of 1–5 nucleotides, the mixture of primers comprising primers having A, G, and C, respectively, present in each position of the 3' end sequence.

The primer may additionally contain a restriction site, usually in the middle of the primer, that may or may not overlap with the oligo(dT) tract. Restriction enzymes and the sites they recognize can be found, for example, in Sambrook et al., 1989, *Molecular Cloning—A Laboratory Manual* (2nd Ed.), Vol. 1, Chapter 5, Cold Spring Harbor Laboratory, Cold Spring Harbor, New York.

The primer for first strand cDNA synthesis may also contain at its 5' end a (arbitrarily) selected sequence of 5–12, 7–9, or 9 nucleotides. This sequence is preferably GC-rich.

The oligonucleotide primers for use in the reactions of the invention can be of any suitable size, and are preferably 24–48 nucleotides in length.

In the method of this invention, it is most preferable to use a 28mer as primer for first-strand cDNA synthesis, the primer being a single-stranded oligonucleotide with a single degenerate base at the 3' end; approximately 14 thymidines located upstream of the degenerate base; a HindIII restriction site upstream of the thymidine tract, wherein the restriction site overlaps the oligo(dT) tract by 2 bases; and a GC-rich tract at the 5' end, wherein the tract consists of 9 arbitrarily selected bases (Zhao et al., *BioTechniques* 24: 842–50, 852, 1998). The primer may be prepared by any suitable methods, such as phosphotriester and phosphodiester methods of synthesis, or automated embodiments thereof. It is also possible to use a primer that has been isolated from a biological source, such as a restriction endonuclease digest, although synthetic primers are preferred.

The primer for first strand cDNA synthesis is annealed to the RNA in a suitable buffer, such as SuperScript™ buffer (Life Technologies, Gaithersburg, Md.), containing 1 mM dithiothreitol (DTT) and 200–250 $\mu$M deoxynucleotide triphosphates (dNTPs) in a volume of approximately 20 $\mu$L. The reaction mixture is added to a temperature between 60° C. and 90° C., preferably about 65° C., for about 5 minutes. The reaction mixture is then allowed to cool to between 37° C. and 55° C., preferably between 37° C. and 42° C., and incubated for approximately 1 hour with reverse transcriptase. The amount of reverse transcriptase employed may vary, but is typically about 80 units/$\mu$g of template. RNase H may be included to help dissociate the RNA:DNA heteroduplex. The reverse transcription reaction is terminated by heating the reaction mixture to 95° C. for about 5 minutes to inactivate the enzyme, then chilling it on ice.

In a specific embodiment, only a single cycle of reverse transcription is carried out. In alternative embodiments, more than one cycle of reverse transcription is performed (with denaturation in between cycles).

Second strand cDNA synthesis is carried out by a method known in the art. By way of example but not limitation: an aliquot of the first-strand cDNA reverse transcribed above is mixed with dNTPs (200–250 $\mu$M each, final concentration) and 1×Klenow reaction buffer (50 mM TRIS-HCl, pH 8.0/10 mM $MgCl_2$/50 mM NaCl) in a final volume of about 20 $\mu$l. Second-strand cDNA synthesis is accomplished by adding Klenow enzyme (3–4 U/reaction; Life Technologies) with an appropriate primer and incubating the mixture at 37° C. for about 45–60 minutes. The Klenow reaction is stopped by incubating the reaction mixture at 65° C. for 5–10 minutes to inactivate the enzyme.

In specific embodiments, the DNA polymerase used for second strand cDNA synthesis is *E. coli* DNA polymerase I, Klenow fragment of *E. coli* DNA polymerase I, or T4 DNA polymerase.

In a preferred embodiment, the primer for second-strand cDNA synthesis anneals within about 200–600 base pairs of the 3' priming site of the first-strand cDNA. The oligonucleotide primers for use in the amplification reactions of the invention can be of any suitable size, and are preferably 24–48 nucleotides in length.

Typically, the primer for second strand cDNA synthesis will be a mixture of primers comprising 1–6 degenerate bases at the 3' end, more often 3–5 degenerate bases, and most often 4 degenerate bases, wherein the degenerate bases may be A, T, G, or C. (Since there are 4 degenerate bases, in theory the primer should hybridize on average $4^4$ or 256 base pairs from the 3' end.) At the 5' end, there may be 8–12 arbitrarily selected bases, preferably 10 arbitrarily selected bases. Between the 3' degenerate bases and the 5' arbitrarily selected bases, there may or may not be a restriction site. In general, it is preferred that the restriction site, if included, be different from the restriction site contained in the oligo(dT) primer used to prime the reverse transcription reaction. The restriction site may overlap with the 5'–10mer by 1–5 bases, preferably 2–3 bases.

Thus, in a specific embodiment, the primer for second strand synthesis is a mixture of primers, each primer comprising at its 5' end a selected sequence of 8–12 nucleotides, and at its 3' end a sequence of 1–6 nucleotides, the mixture of primers comprising primers having A, G, C and T, respectively, present in each position of the 3' end sequence.

In the method of the invention, it is preferred to use a single-stranded 28mer primer for second strand synthesis such as FP#1 (see FIG. 1), with 4 degenerate bases at its 3' end; 10 arbitrarily selected bases at its 5' end; and an XbaI restriction site disposed upstream from the degenerate bases, wherein the restriction site overlaps with the 5' 10mer by 2 bases. The primer can be synthesized as described above for the oligo(dT) primer.

5.5. METHODS OF NUCLEIC ACID AMPLIFICATION USING RNAP-CONTAINING PRIMERS OF THE INVENTION

The methods of the present invention may be applied to amplification systems in which an oligonucleotide is incorporated into an amplification product such as polymerase chain reaction (PCR) systems (U.S. Pat. No. 4,683,195, Mullis et al., entitled "Process for amplifying, detecting, and/or-cloning nucleic acid sequences," issued Jul. 28, 1987; U.S. Pat. No. 4,683,202, Mullis, entitled "Process for amplifying nucleic acid sequences," issued Jul. 28, 1987). As a result of amplification, the RNAP-containing primers are incorporated into the double-stranded polynucleotide amplification products.

RNAP-containing primers may be employed in any amplification method in which the RNAP-containing primer is not complementary to any other oligonucleotide used in the reaction mixture, and in which the RNAP-containing primer is incorporated into a double-stranded DNA amplification product, e.g., PCR.

In one embodiment, the primers of the invention are used to prime an amplification in situ, on samples of preserved or fresh cells or tissues (see, e.g., Nuovo, 1997, *PCR In Situ Hybridization: Protocols and Applications, Third Edition*, Lippincott-Raven Press, New York).

In one embodiment, the invention is directed to a method for amplifying at least one mRNA in a sample containing a plurality of different mRNAs comprising (a) synthesizing first strand cDNA by contacting under conditions conducive to reverse transcriptase activity at least one mRNA in said sample with (i) reverse transcriptase, and (ii) a first primer that is sufficiently complementary to a sequence in or adjacent to the poly A tail in the mRNA so as to prime synthesis in a direction toward the 5' end of the mRNA; (b) synthesizing double-stranded cDNA by contacting under conditions conducive to DNA polymerase activity the first strand cDNA with (i) a first DNA polymerase, and (ii) a second primer that is sufficiently complementary to a sequence 5' to said first primer sequence in said first strand cDNA so as to prime synthesis in a direction toward said first primer sequence; wherein neither said first primer nor said second primer comprises an RNA polymerase promoter sequence in sense or antisense orientation; (c) amplifying the double-stranded cDNA by subjecting the double-stranded cDNA to a single round of polymerase chain reaction (hereinafter "PCR") of 20 cycles or less, wherein DNA is synthesized by use of a second DNA polymerase and a primer pair comprising a forward primer and a reverse primer, said forward primer and said reverse primer each being sufficiently complementary to a different strand of said double-stranded cDNA so as to prime synthesis in a template-dependent manner, wherein said forward primer or reverse primer comprises an RNA polymerase promoter sequence in sense or antisense orientation; and (d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced.

The method of this invention involves the incorporation of an RNA polymerase promoter (RNAP) into ds cDNA by priming cDNA amplification by PCR with a primer comprising a synthetic oligonucleotide containing the promoter sequence in sense or antisense orientation ("RNAP-containing primer"). Following multiple cycles of PCR, the resultant RNAP-containing ds cDNA is transcribed into RNA using an RNA polymerase capable of binding to the RNAP introduced during cDNA synthesis. The number of cycles of PCR performed is limited so as to preserve sequence and transcript representation fidelity, while still affording a modest degree of amplification. Generally, only a single round of PCR is performed, of no more than 20, 15, 10, or 5 cycles (of denaturation). Additional, linear amplification is afforded by the in vitro transcription step. This combination of PCR and IVT enables the generation of a relatively large amount of cRNA from a small starting number of cells without loss of fidelity. RNAs generated using this method may be labeled and employed to profile gene expression in different populations of cells.

In a preferred embodiment, RNA amplified by the methods of this invention is suitable for quantitative comparisons of gene expression between different populations of cells or between populations of cells exposed to different stimuli.

5.5.1. METHODS OF USE OF RNAP-CONTAINING PRIMERS IN POLYMERASE CHAIN REACTION (PCR)

The RNAP-containing primers of the invention are used to prime a polymerase chain reaction (PCR), thereby becoming incorporated into the amplification product (FIG. 1). The forward primer and/or the reverse primer may be an RNAP-containing primer. The forward and reverse primers differ in sequence from the primer for first strand cDNA synthesis and the primer for second strand DNA synthesis.

The reverse primer hybridizes to a region of the ds DNA that is downstream from the region to which the forward primer hybridizes.

In order for the cDNAs amplified in this step to be useful in the methods of the invention, it is necessary to incorporate an RNAP into the cDNA molecules during synthesis. This enables them to serve as templates for RNA transcription following amplification by PCR. This is accomplished by choosing one or more primers for the PCR reaction that comprise a single-stranded, synthetic oligonucleotide containing an RNAP. Preferably, the RNAP is located at or near the 5' terminus of the primer, in an orientation permitting transcription of the RNA population under study. The RNAP is preferably derived from a prokaryote, such as *E. coli* or the bacteriophage T7, SP6, and T3, with the T7 RNAP particularly preferred.

Typically, only one RNAP-containing primer is used during PCR amplification. The RNAP-containing primer preferably binds to or near the 3'- or 5'-end of the cDNAs. Generally, it is chosen to bind to the 3' end.

In preferred embodiments, in order to amplify all or substantially all the double-stranded cDNA in the sample, the forward primer used in PCR comprises a 3' end sequence that is the same as the 5' end sequence of the primer used to prime second strand cDNA synthesis, and the reverse primer used in PCR comprises a 3' end sequence that is the same as the 5' end sequence of the primer used to prime first strand cDNA synthesis. Either the forward primer or reverse primer further comprises a sequence of an RNA polymerase promoter in sense or antisense orientation, which promoter sequence is situated 5' to these sequences found in the first or second strand cDNA synthesis primers.

Representative 3'-end primers containing the T7 RNAP are RP#3 and FP#3. Reverse primer RP#3 hybridizes to the 3' end of the sense strand of the ds cDNA. The sequence of the T7 RNA polymerase promoter (T7RNAP) is highlighted in bold:

RP#3 5' TAA TAC GAC TCA CTA TAG GGA GGA CCT CCT GCG AAG CTT TTT TTT TTT TTT 3' (SEQ ID NO:3)

RP#3 is useful for introducing an RNAP for transcription-based amplification of antisense RNA.

Forward primer FP#3 hybridizes to the 3' end of the first strand cDNA or the antisense strand of ds cDNA. The sequence of the T7 RNA polymerase promoter (T7RNAP) is highlighted in bold:

FP#3 5' TAA TAC GAC TCA CTA TAG GGA GGA GTT CGA GAC CTC TAG ATG CTG TTG 3' (SEQ ID NO:6)

Since forward primer FP#3 hybridizes to the 3' end of the first strand cDNA or the antisense strand of ds cDNA, it may be used in place of FP#2 (SEQ ID NO:5) when sense strand RNA is desired.

PCR amplification of ds cDNA is performed according to methods well-known in the art. Any one of several thermostable polymerases, such as Taq, rTth, or Vent$_R$®, may be employed. These are commercially available from a variety of sources, including Perkin-Elmer-Cetus (Norwalk, Conn.), United States Biochemical Corp. (Cleveland, Ohio), Beckman Instruments (Fullerton, Calif.), and Amersham Corp. (Arlington Heights, Ill.). The number of cycles employed may vary, but in the present invention typically less than 25, more often less than 15, and most often about 10 cycles are preferred. The optimal number of cycles to be performed can be determined empirically, for example, using the method described in Section 6 (Example 1) below.

5.5.2. METHODS OF USE OF RNAP-CONTAINING PRIMERS IN ALLELE-SPECIFIC PCR (ASP)

In another embodiment, primers of the invention are used to prime an allele-specific PCR (ASP) (PCT International Publication No. WO9802449, published Jan. 22, 1998). In this embodiment, one or both amplification primers may be RNAP-containing primers. In ASP, a target DNA is preferentially amplified if it is completely complementary to the 3' end of a PCR amplification primer. The 3' end of the primer should terminate at or within one or 2 bases of a known mutation site in a gene (target DNA) to which it has a complementary sequence. Under the appropriate reaction conditions, the target DNA is not amplified if there is a base mismatch (e.g., a nucleotide substitution caused by a mutation) or a small deletion or insertion, at the 3' end of the primer (Okayama et al., 1989, J. Lab. Clin. Med. 114:105–113; Sommer et al., 1992, BioTechniques 12:82–87). Thus, ASP can be used to detect the presence or absence of at least a single mismatch between the primer sequence that is complementary to the preselected target sequence and a nucleic acid in the sample; amplification indicates the absence of such a single mismatch.

5.6. IN VITRO TRANSCRIPTION (IVT) OF cDNA

Following PCR amplification of ds cDNAs using one or more primers comprising a synthetic oligonucleotide containing an RNAP, the cDNA mixture is incubated with an appropriate RNA polymerase enzyme to drive transcription from the RNAP. The RNA polymerase used for transcription must be capable of binding to the particular RNAP contained in the primer; hence usually the RNAP and the polymerase will be homologous. For example, if the T7 RNAP is employed in the primer, it is preferred to use T7 RNA polymerase to drive transcription. T7 polymerase is commercially available from several sources, including Promega Biotech (Madison, Wis.) and Epicenter Technologies (Madison, Wis.).

The incubation time may be varied depending upon how many transcripts it is desired to generate. Usually, an incubation time of 30–90 minutes will suffice. A longer time may be preferable, however, if fewer than 10 cycles of PCR are performed, while a shorter time may suffice if more than 15–20 cycles of PCR are performed. In general, it is preferred to optimize the method by lengthening the IVT step rather than by increasing the number of cycles of PCR, since the latter results in lower sequence and transcript representation fidelity.

5.7. METHODS FOR DETERMINING BIOLOGICAL RESPONSE PROFILES

In one embodiment, the invention is directed to a method for comparing the presence or amount of at least one mRNA of interest in a first sample and in a second sample, said first sample and said second sample each containing a plurality of different mRNAs from one or more cells, comprising: (a) synthesizing first strand cDNA by contacting under conditions conducive to reverse transcriptase activity at least one mRNA in said first sample with (i) reverse transcriptase, and (ii) a first primer that is sufficiently complementary to a sequence in or adjacent to the poly A tail in the mRNA so as to prime synthesis towards the 5' end of the mRNA; (b) synthesizing double-stranded cDNA by contacting under conditions conducive to DNA polymerase activity the first strand cDNA with (i) a DNA polymerase, and (ii) a second primer that is sufficiently complementary to a sequence 5' to said first primer sequence in said first strand cDNA so as to prime synthesis toward said first primer sequence; (c) amplifying the double-stranded cDNA by subjecting the double-stranded cDNA to a single round of PCR of 20 cycles or less, wherein DNA is synthesized by use of a DNA polymerase and a primer pair comprising a forward primer and a reverse primer, said forward primer and said reverse primer each being sufficiently complementary to a different strand of said double-stranded cDNA so as to prime synthesis in a template-dependent manner, wherein said forward primer or reverse primer comprises an RNA polymerase promoter sequence in sense or antisense orientation; (d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced; (e) labeling the cRNA produced in step (d) with a first label; (f) repeating steps (a)–(d) with said second sample; (g) labeling the cRNA produced in step (f) with a second label distinguishable from said first label; (h) detecting or measuring the mRNA of interest in the first sample by contacting the cRNA labeled with said first label with a polynucleotide probe capable of hybridizing to said cRNA of the mRNA of interest under conditions conducive to hybridization; and detecting any hybridization that occurs between said probe and said cRNA; (i) detecting or measuring the mRNA of interest in the second sample by contacting the cRNA labeled with said second label with said polynucleotide probe capable of hybridizing to said cRNA of the mRNA of interest under conditions conducive to hybridization; and detecting any hybridization that occurs between said probe and said cRNA; and (j) comparing the mRNA of interest detected or measured in said first sample with the mRNA of interest detected or measured in said second sample.

The invention utilizes the ability to measure the responses of a biological system to a large variety of perturbations. This section provides some exemplary methods for measuring biological responses. One of skill in the art would appreciate that this invention is not limited to the following specific methods for measuring the responses of a biological system. In particular, the presence of cRNA(s) of interest (and thus mRNA(s) of interest in the sample) can be detected or measured by procedures including but not limited to Northern blotting or using bead-bound oligonucleotides as probes, or the use of polynucleotide microarrays.

In a specific embodiment of the invention, one or more labels is introduced into the RNA during the transcription step to facilitate gene expression profiling. Gene expression can be profiled in any of several ways, among which the preferred method is to probe a DNA microarray with the labeled RNA transcripts generated above. A DNA microarray, or chip, is a microscopic array of DNA fragments or synthetic oligonucleotides, disposed in a defined pattern on a solid support, wherein they are amenable to analysis by standard hybridization methods (Schena, *BioEssays* 18: 427, 1996).

The DNA in a microarray may be derived from genomic or cDNA libraries, from fully sequenced clones, or from partially sequenced cDNAs known as expressed sequence tags (ESTs). Methods for obtaining such DNA molecules are generally known in the art (see, e.g.,Ausubel et al., eds., 1994, *Current Protocols in Molecular Biology*, vol. 2, Current Protocols Publishing, New York). Alternatively, oligonucleotides may be synthesized by conventional methods, such as phosphoramidite-based synthesis.

Gene expression profiling can be done for purposes of screening, diagnosis, staging a disease, and monitoring response to therapy, as well as for identifying genetic targets of drugs and of pathogens.

5.7.1. TRANSCRIPT ASSAY USING DNA ARRAYS

This invention is particularly useful for the analysis of gene expression profiles. For expression profiling, DNA microarrays are typically probed using mRNA, extracted and amplified from the cells whose gene expression profile it is desired to analyze, using the 3'-end PCR/IVT amplification method of the invention. To facilitate comparison between any two samples of interest, the mRNAs are typically labeled separately with fluorescent dyes that emit at different wavelengths, as described in Section 5.2. Some embodiments of this invention are based on measuring the transcriptional rate of genes.

The transcriptional rate can be measured by techniques of hybridization to arrays of nucleic acid or nucleic acid mimic probes, described in the next subsection, or by other gene expression technologies, such as those described in the subsequent subsection. However measured, the result is either the absolute, relative amounts of transcripts or response data including values representing RNA abundance ratios, which usually reflect DNA expression ratios (in the absence of differences in RNA degradation rates).

In various alternative embodiments of the present invention, aspects of the biological state other than the transcriptional state, such as the translational state, the activity state, or mixed aspects can be measured.

Preferably, measurement of the transcriptional state is made by hybridization to transcript arrays, which are described in this subsection. Certain other methods of transcriptional state measurement are described later in this subsection.

In a preferred embodiment the present invention makes use of "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cRNA that is amplified by the methods of the present invention) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

In one embodiment, the microarray is an array of polynucleotide probes, the array comprising a support with at least one surface and at least 100 different polynucleotide probes, each different polynucleotide probe comprising a different nucleotide sequence and being attached to the surface of the support in a different location on the surface. Preferably, the nucleotide sequence of each of the different polynucleotide probes is in the range of 40 to 80 nucleotides in length. More preferably, the nucleotide sequence of each of the different polynucleotide probes is in the range of 50 to 70 nucleotides in length. Even more preferably, the nucleotide sequence of each of the different polynucleotide probes is in the range of 50 to 60 nucleotides in length.

In specific embodiments, the array comprises polynucleotide probes of at least 2,000, 4,000, 10,000, 15,000, 20,000, 50,000, 80,000, or 100,000 different nucleotide sequences.

In another embodiment, the nucleotide sequence of each polynucleotide probe in the array is specific for a particular target polynucleotide sequence. In yet another embodiment, the target polynucleotide sequences comprise expressed polynucleotide sequences of a cell or organism.

In a specific embodiment, the cell or organism is a mammalian cell or organism. In another specific embodiment, the cell or organism is a human cell or organism.

In specific embodiments, the nucleotide sequences of the different polynucleotide probes of the array are specific for at least 50%, at least 75%, at least 80%, at least 85%, at least 90%, at least 95%, or at least 99% of the genes in the genome of the cell or organism. Most preferably, the nucleotide sequences of the different polynucleotide probes of the array are specific for all of the genes in the genome of the cell or organism.

In specific embodiments, the polynucleotide probes of the array hybridize specifically and distinguishably to at least 10,000, to at least 20,000, to at least 50,000, different polynucleotide sequences, to at least 80,000, or to at least 100,000 different polynucleotide sequences.

In other specific embodiments, the polynucleotide probes of the array hybridize specifically and distinguishably to at least 90%, at least 95%, or at least 99% of the genes or gene transcripts of the genome of a cell or organism. Most preferably, the polynucleotide probes of the array hybridize specifically and distinguishably to the genes or gene transcripts of the entire genome of a cell or organism.

In specific embodiments, the array has at least 100, at least 250, at least 1,000, or at least 2,500 probes per 1 cm$^2$, preferably all or at least 25% or 50% of which are different from each other.

In another embodiment, the array is a positionally addressable array (in that the sequence of the polynucleotide probe at each position is known).

In another embodiment, the nucleotide sequence of each polynucleotide probe in the array is a DNA sequence. In another embodiment, the DNA sequence is a single-stranded DNA sequence. The DNA sequence may be, e.g., a cDNA sequence, or a synthetic sequence.

It will be appreciated that when cRNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cRNAs from two different cells are hybridized to the binding sites of the microarray. In the case of drug responses one biological sample is exposed to a drug and another biological sample of the same type is not exposed to the drug. In the case of pathway responses one cell is exposed to a pathway perturbation and another cell of the same type is not exposed to the pathway perturbation. The cRNA derived from each of the two cell types are differently labeled so that they can be distinguished. In one embodiment, for example, cRNA from a cell treated with a drug (or exposed to a pathway perturbation) is synthesized using a fluorescein-labeled NTP, and cRNA from a second cell, not drug-exposed, is synthesized using a rhodamine-labeled NTP. When the two cRNAs are mixed and hybridized to the microarray, the relative intensity of signal from each cRNA set is determined for each site on the array, and any relative difference in abundance of a particular mRNA detected.

In the example described above, the cRNA from the drug-treated (or pathway perturbed) cell will fluoresce green when the fluorophore is stimulated and the cRNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cRNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., 1995, Science 270:467–470, which is incorporated by reference in its entirety for all purposes. An advantage of using cRNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cRNA from a single cell, and compare, for example, the absolute amount of a particular mRNA in, e.g., a drug-treated or pathway-perturbed cell and an untreated cell.

5.7.2. PREPARATION OF MICROARRAYS

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cRNA can specifically hybridize. The nucleic acid or analogue of the binding site can be, e.g., a synthetic oligomer, a full-length cRNA, a less-than full length cRNA, or a gene fragment.

In one embodiment, the microarray contains binding sites for products of all or almost all genes in the target organism's genome. This microarray will have binding sites corresponding to at least about 50% of the genes in the genome, often at least about 75%, more often at least about 85%, even more often more than about 90%, and most often at least about 99%.

Such comprehensiveness, however, is not necessarily required. In another embodiment, the microarray contains binding sites for products of human genes. This microarray will have binding sites corresponding to at least about 5–10% of the genes in the genome, preferably at least about 10–15%, and more preferably at least about 40%.

Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Science 274:546–567, which is incorporated by reference in its entirety for all purposes). In contrast, the human genome is estimated to contain approximately $10^5$ genes.

5.7.3. PREPARATION OF NUCLEIC ACIDS FOR MICROARRAYS

As noted above, the "binding site" to which a particular cognate cRNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e., fragments that do not share more than bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length.

PCR methods are well known and are described, for example, in Innis et al., eds., 1990, *PCR Protocols: A Guide to Methods and Applications*, Academic Press Inc., San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (e.g., Froehler et al., 1986, Nucleic Acid Res 14:5399–5407). Synthetic sequences are between about 15 and about 100 bases in length, preferably between about 20 and about 50 bases.

In some embodiments, synthetic nucleic acids include non-natural bases, e.g., inosine. Where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone. The making of such modifications is within the skill of one trained in the art.

As noted above, nucleic acid analogues may be used as binding sites for hybridization. An example of a suitable nucleic acid analogue is peptide nucleic acid (see, e.g., Egholm et al., 1993, Nature 365:566–568; see also U.S. Pat. No. 5,539,083, Cook et al., entitled "Peptide nucleic acid combinatorial libraries and improved methods of synthesis," issued Jul. 23, 1996).

In an alternative embodiment, the binding (hybridization) sites are made from plasmid or phage clones of genes, cDNAs (e.g., expressed sequence tags), or inserts therefrom (Nguyen et al., 1995, Genomics 29:207–209). In yet another embodiment, the polynucleotide of the binding sites is RNA.

5.7.4. ATTACHING NUCLEIC ACIDS TO THE SOLID SURFACE

The nucleic acid or analogue are attached to a solid support, which may be made from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. Preferably, the glass support is treated with polylysine or silane to facilitate attachment of oligonucleotides to the slide.

Methods of immobilizing DNA on the solid support may include direct touch, micropipetting (Yershov et al., Proc. Natl. Acad. Sci. USA (1996) 93(10):4913–4918), or the use of controlled electric fields to direct a given oligonucleotide to a specific spot in the array (U.S. Pat. No. 5,605,662, Heller et al., entitled "Active programmable electronic devices for molecular biological analysis and diagnostics," issued Feb. 25, 1997). DNA is typically immobilized at a density of 100 to 10,000 oligonucleotides per $cm^2$ and preferably at a density of about 1000 oligonucleotides per $cm^2$.

A preferred method for attaching the nucleic acids to a surface is by printing on glass plates, as is described generally by Schena et al., 1995, Science 270:467–470. This method is especially useful for preparing microarrays of cDNA. See also DeRisi et al., 1996, Nature Genetics 14:457–460; Shalon et al., 1996, Genome Res. 6:639–645; and Schena et al., Proc. Natl. Acad. Sci. USA, 1996, 93(20):10614–19.)

In a preferred alternative to immobilizing pre-fabricated oligonucleotides onto a solid support, it is possible to synthesize oligonucleotides directly on the support (Maskos et al., Nucl. Acids Res. 21: 2269–70, 1993; Fodor et al., Science 251: 767–73, 1991; Lipshutz et al., 1999, Nat. Genet. 21(1 Suppl):20–4). Among methods of synthesizing oligonucleotides directly on a solid support, particularly preferred methods are photolithography (see Fodor et al., Science 251: 767–73, 1991; McGall et al., Proc. Natl. Acad. Sci. (USA) 93: 13555–60, 1996) and piezoelectric printing (Lipshutz et al., 1999, Nat. Genet. 21(1 Suppl):20–4), with the piezoelectric method most preferred.

In one embodiment, a high-density oligonucleotide array is employed. Techniques are known for producing arrays containing thousands of oligonucleotides complementary to defined sequences, at defined locations on a surface using photolithographic techniques for synthesis in situ (see, Fodor et al., 1991, Science 251:767–773; Pease et al., 1994, Proc. Natl. Acad. Sci. USA 91:5022–5026; Lockhart et al., 1996, Nature Biotechnol. 14:1675–80; U.S. Pat. No. 5,578,832, Trulson et al., entitled "Method and apparatus for imaging a sample on a device," issued Nov. 26, 1996; U.S. Pat. No. 5,556,752, Lockhart et al., entitled "Surface-bound, unimolecular, double-stranded DNA," issued Sep. 17, 1996; and U.S. Pat. No. 5,510,270, Fodor et al., entitled "Synthesis and screening of immobilized oligonucleotide arrays," issued Apr. 23, 1996; each of which is incorporated by reference in its entirety for all purposes) or other methods for rapid synthesis and deposition of defined oligonucleotides (Lipshutz et al., 1999, Nat. Genet. 21(1 Suppl):20–4.)

When these methods are used, oligonucleotides (e.g., 20-mers) of known sequence are synthesized directly on a surface such as a derivatized glass slide. Usually, the array produced contains multiple probes against each target transcript. Oligonucleotide probes can be chosen to detect alternatively spliced mRNAs or to serve as various type of control.

Another preferred method of making microarrays is by use of an inkjet printing process to synthesize oligonucleotides directly on a solid phase, as described, e.g., in co-pending U.S. patent application Ser. No. 09/008,120 filed on Jan. 16, 1998, by Blanchard entitled "Chemical Synthesis Using Solvent Microdroplets", which is incorporated by reference herein in its entirety.

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., 1989, *Molecular Cloning—A Laboratory Manual* (2nd Ed.), Vols. 1–3, Cold Spring Harbor Laboratory, Cold Spring Harbor, N.Y.), could be used, although, as will be recognized by those of skill in the art, very small arrays will be preferred because hybridization volumes will be smaller.

5.7.5. HYBRIDIZATION TO MICROARRAYS

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., 1996, Genome Research 6:639–645, and Chee et al., 1996, Science 274:610–614).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al. (1989, *Molecular Cloning—A Laboratory Manual* (2nd Ed.), Vols. 1–3, Cold Spring Harbor Laboratory, Cold Spring Harbor, N.Y.) and in Ausubel et al. (1987, *Current Protocols in Molecular Biology*, Greene Publishing, Media, Pa., and Wiley-Interscience, New York). When the cDNA microarrays of Schena et al. (1996, Proc. Natl. Acad. Sci. USA, 93:10614–19) are used, typical hybridization conditions are hybridization in 533 SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Schena et al., 1996, Proc. Natl. Acad. Sci. USA, 93:10614–19). Useful hybridization conditions are also provided in, e.g.,Tijssen, 1993, *Hybridization With Nucleic Acid Probes*, Elsevier Science Publishers B.V., Amsterdam and New York, and Kricka, 1992, *Nonisotopic DNA Probe Techniques*, Academic Press, San Diego, Calif.

Although simultaneous hybridization of differentially labeled mRNA samples is preferred, it is also possible to use a single label and to perform hybridizations sequentially rather than simultaneously.

5.7.6. SIGNAL DETECTION AND DATA ANALYSIS

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Research 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Shalon et al., 1996, Genome Res. 6:639–645 and in other references cited herein. Alternatively, the fiber-optic bundle described by Ferguson et al., 1996, Nature Biotechnol. 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two biological samples is scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In one embodiment, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are described in e.g., co-pending U.S. patent applications Ser. No. 09/179,569 filed on Oct. 27, 1998, by Friend et al.; Ser. No. 09/220,142 filed on Dec. 23, 1998, by Stoughton et al.; Ser. No. 09/220,275 filed on Dec. 23, 1998, by Friend et al.; which are incorporated by reference herein in their entireties.

5.8. DIAGNOSTIC METHODS

The oligonucleotides of the invention have use in nucleic acid amplification reactions, as primers, to detect or measure a nucleic acid product of the amplification, thereby detecting or measuring a target nucleic acid in a sample that is complementary to a 3' primer sequence. Accordingly, the oligonucleotides of the invention can be used in methods of diagnosis, wherein a 3' primer sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human or animal, or of a microorganism, etc. In another embodiment that can be used in the diagnosis or prognosis of a disease or disorder, the target sequence is a wild type human genomic or RNA or cDNA sequence, mutation of which is implicated in the presence of a human disease or disorder, or alternatively, can be the mutated sequence. In such an embodiment, optionally, the amplification reaction can be repeated for the same sample with different sets of primers that amplify, respectively, the wild type sequence or the mutated version. By way of example, the mutation can be an insertion, substitution, and/or deletion of one or more nucleotides, or a translocation.

5.9. KITS FOR THE AMPLIFICATION AND DETECTION of Selected Target Nucleotide Sequences An additional aspect of the present invention relates to kits for the detection or measurement of nucleic acid amplification products and for determining the responses or state of a biological sample. In specific embodiments, the kits comprise one or more primer oligonucleotides of the invention, such as an RNAP-containing primer, including but not limited to an RNAP-containing primer and/or a non-RNAP-containing primer, in one or more containers. The kit can further comprise additional components for carrying out the amplification reactions of the invention. Where the target nucleic acid sequence being amplified is one implicated in disease or disorder, the kits can be used for diagnosis or prognosis. In a specific embodiment, a kit is provided that comprises, in one or more containers, forward and reverse primers of the invention for carrying out amplification, and optionally, a DNA polymerase.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers.

In a specific embodiment, a kit comprises, in one or more containers, a pair of primers that are preferably 24–48 nucleotides in length and that are capable of priming amplification [e.g., by polymerase chain reaction (see e.g., Innis et al., eds., 1990, *PCR Protocols: A Guide to Methods and Applications,* Academic Press Inc., San Diego, Calif.), for example, competitive PCR and competitive reverse-transcriptase PCR (Clementi et al., 1994, Genet. Anal. Tech. Appl. 11(1):1–6; Siebert et al., 1992, Nature 359:557–558), under appropriate reaction conditions, of at least a portion of a selected target nucleic acid.

In another embodiment, a kit comprises in one or more containers a mixture of first primers, each first primer comprising an oligo (dT) sequence and a 3' end sequence of 1–5 nucleotides, and said mixture of first primers comprising primers having A, G, and C, respectively, present in each position of said 3' end sequence.

In another embodiment, a kit comprises in one or more containers (a) a mixture of first primers, each first primer comprising a 3' end sequence of 1–5 nucleotides, and said mixture of first primers comprising primers having A, G, and C, respectively, present in each position of said 3' end sequence, wherein each primer in said mixture of first primers further comprises at its 5' end an identical selected sequence of 5–12 nucleotides and optionally further comprises an oligo (dT) sequence situated between said 5' end sequence and said 3' end sequence; (b) a mixture of second primers, each second primer comprising at its 5' end an identical selected sequence of 8–12 nucleotides, and at its 3' end a sequence of 1–6 nucleotides, said mixture of second primers comprising primers having A, G, C and T, respectively, present in each position of said 3' end sequence; wherein neither said first primer nor said second primer comprises an RNA polymerase promoter sequence in sense or antisense orientation; and (c) a primer pair suitable for use in PCR, said primer pair comprising a forward primer and a reverse primer, wherein said forward primer or reverse primer comprises an RNA polymerase promoter sequence in sense or antisense orientation.

In one embodiment of the above kit, the forward primer comprises the RNA polymerase promoter sequence.

In another embodiment of the above kit, the reverse primer comprises the RNA polymerase promoter sequence.

In a particular embodiment, the forward primer in the kit comprises a 3' end sequence that is the same as the 5' end sequence of the second primer, and the reverse primer comprises a 3' end sequence that is the same as the 5' end sequence of the first primer.

The kit optionally further comprises in a separate container an RNA polymerase specific to the RNA polymerase promoter, and/or a buffer for PCR, and/or a DNA polymerase.

The kit optionally further comprises a set of directions for carrying out PCR; and a set of directions for carrying out transcribing of amplified double-stranded cDNA into cRNA.

The kit optionally further comprises a control nucleic acid, and/or a microarray, and/or means for stimulating and detecting fluorescent light emissions from fluorescently labeled RNA, and/or expression profile projection and analysis software capable of being loaded into the memory of a computer system.

In another embodiment, a kit for the detection of a selected target DNA target sequence comprises in one or more containers (a) PCR primers, one or both of which are RNAP-containing primers; and optionally: (b) a control DNA target sequence; (c) an optimized buffer for amplification; (d) appropriate enzymes for the method of amplification contemplated, e.g., a DNA polymerase for PCR; (d) a set of directions for carrying out amplification, e.g., describing the optimal conditions, e.g., temperature, number of cycles for amplification. Optionally, the kit provides (e) means for stimulating and detecting fluorescent light emissions, e.g., a fluorescence plate reader or a combination thermocycler-plate-reader to perform the analysis.

5.9.1. ANALYTIC KIT IMPLEMENTATION

In a preferred embodiment, the methods of this invention can be implemented by use of kits containing oligonucleotide primers of the invention and microarrays. The microarrays contained in such kits comprise a solid phase, e.g, a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations to the particular protein whose activity is determined by the kit. The probes contained in the kits of this invention preferably substantially exclude nucleic acids which hybridize to RNA species that are not increased in response to perturbations to the particular protein whose activity is determined by the kit.

In another preferred embodiment, a kit of the invention further contains expression profile projection and analysis software capable of being loaded into the memory of a computer system. An example of such a system is described in co-pending U.S. patent application Ser. No. 09/220,276, by Bassett, Jr. et al., filed Dec. 23, 1998, which is incorporated herein by reference in its entirety. Preferably, the expression profile analysis software contained in a kit of this invention, is essentially identical to the expression profile analysis software 512 described in U.S. patent application Ser. No. 09/220,276.

Alternative kits for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

The following experimental examples are offered by way of illustration and not by way of limitation.

6. EXAMPLE 1

Numerous Cycles of PCR Amplification of mRNA from Yeast Introduce Biases

This example demonstrates that increasing cycles of PCR amplification introduce more biases, i.e., differences between replicate samples that limit transcript representation fidelity.

6.1 MATERIALS AND METHODS

The sequences of reverse primers RP#1, RP#2 and RP#3 were overlapping and designed to hybridize to the same sequence.

Reverse primer RP#1 hybridizes to the 3' end of mRNA. RP#1 primer contains one degenerate base (V) as an anchor at its 3' end. The degenerate base may be A, G, or C.

RP#1 5' CCT CCT GCG AAG CTT TTT TTT TTT TTT V 3' (SEQ ID NO:1)

where V=A, G, or C.

Reverse primer RP#2 hybridizes to the 3' end of the sense strand of the ds cDNA:

RP#2 5' CCT CCT GCG AAG CTT TTT TTT TTT TTT 3' (SEQ ID NO:2)

Reverse primer RP#3 hybridizes to the 3' end of the sense strand of the ds cDNA:

RP#3 5' TAA TAC GAC TCA CTA TAG GGA GGA CCT CCT GCG AAG CTT TTT TTT TTT TTT 3' (SEQ ID NO:3)

RP#3 is a representative 3'-end primer containing the T7 RNAP. RP#3 is useful for introducing an RNAP for transcription-based amplification of antisense RNA. The sequence of the T7 RNA polymerase promoter (T7RNAP) is highlighted in bold.

The sequences of forward primers FP#1, FP#2 and FP#3 were overlapping and designed to hybridize to the same sequence.

Forward primer FP#1 hybridizes to the 3' end of the first-strand cDNA:

FP#1 5' GTT CGA GAC CTC TAG ATG CTG TTG NNN N 3' (SEQ ID NO:4)

where N=A, T, G, or C.

Forward primer FP#2 hybridizes to the 3' end of the first strand cDNA or the antisense strand of ds cDNA.

FP#2 5' GTT CGA GAC CTC TAG ATG CTG TTG 3' (SEQ ID NO:5)

Forward primer FP#3 hybridizes to the 3' end of the first strand cDNA or the antisense strand of ds cDNA. The sequence of the T7 RNA polymerase promoter (T7RNAP) is highlighted in bold:

FP#3 5' TAA TAC GAC TCA CTA TAG GGA GGA GTT CGA GAC CTC TAG ATG CTG TTG 3' (SEQ ID NO:6)

Since forward primer FP#3 hybridizes to the 3' end of the first strand cDNA or the antisense strand of ds cDNA, it may be used in place of FP#2 when sense strand RNA is desired.

Total cellular RNA was prepared from wild type (wt) yeast *Saccharomyces cerevisiae* as described by Marton et al. (Nature Med. 4: 1293–1301, 1998). RNA was amplified using the 3' end PCR/IVT method of the invention. Briefly, RNA was reverse transcribed using RP#1 and converted to dsDNA using the Klenow enzyme and FP#1, followed by PCR amplification.

The number of cycles of PCR performed varied between 10 and 25. For each cycle number, two 3'-end PCR pools were prepared in parallel using FP#2 and RP#3. The IVT step was then performed, in which the PCR-amplified cDNAs were transcribed into RNA by reaction with T7 RNA polymerase for 16 hours at 37° C. The RNAP promoter introduced during the PCR step supported the transcription of sense RNA from the cDNAs. RNAs were labeled during the IVT step by the inclusion of allylamine-derivatized UTP. Following IVT, unreacted NTPs were removed by using gel filtration or an RNeasy® Mini kit (QIAGEN Inc.—USA, Valencia, Calif.).

The cRNAs were fluorescently labeled with the NHS esters of Cy3 and Cy5 ("Cy Dyes," Amersham Life Sciences, Pittsburgh, Pa.), using a two-step procedure in which allylamine-derivatized UTP is incorporated during IVT. While cRNA produced by PCR/IVT is designed to be used for two color hybridization to DNA microarrays, there are few readily available methods for preparing cRNAs labeled with different fluorescent dyes. The most obvious method of labeling cRNA is to include labeled nucleotides during the in vitro transcription with RNAP. However, to prepare high specific activity labeled cRNA by in vitro transcription, the labeled nucleotides must be available at high concentration (typically 75 mM). This is possible only in certain cases, such as with biotinylated nucleotides, where the labeled nucleotide is relatively cheap and available in high concentration. In most cases, preparation of suitable concentrations of fluorescently labeled nucleotide would be prohibitively expensive. The method of the present invention for preparing fluorescent-labeled cRNA is relatively inexpensive and suitable for use in two color hybridizations to DNA microarrays.

In the first step, aminoallyl (AA)-labeled nucleic acids were prepared by incorporation of AA-nucleotides. AA-UTP (Sigma A-5660) was used for labeling the cRNA. AA-cRNA was prepared using the Ambion MegaScript T7 RNA polymerase in vitro transcription kit, with AA-UTP substituted at 50–100% of the total UTP concentration. It is essential to remove all traces of amine-containing buffers such as Tris prior to derivatizing the AA-nucleic acids. AA-nucleic acids prepared in enzymatic reactions were cleaned up on appropriate QIAGEN columns: RNeasy® Mini kit (for RNA) or QIAquick PCR Amplification kit (for DNA) (QIAGEN Inc.—USA, Valencia, Calif.). For the QIAGEN columns, samples were applied twice. For washes, 80% EtOH was substituted for the buffer provided with the QIAGEN kit. Samples were eluted twice with 50 µl volumes of 70° C. $H_2O$.

In the second step, AA-nucleic acids were derivatized with either Cy 3 or Cy 5 NHS-ester. 2–6 µg of AA-labeled nucleic acid were aliquoted into a microfuge tube, adjusting the total volume to 12 µl with $H_2O$. The NHS-ester was dissolved at a concentration of ~15 mM in anhydrous DMSO (~200 nmoles in 13 µl). 27 µl of 0.1 M sodium carbonate buffer, pH 9, was added. 12 µl of the dye mix (containing ~60 nmoles dye-NHS ester) was then immediately added to the AA-labeled nucleic acid (~6–20 pmoles of a 1 kb molecule). The samples were then incubated in the dark at 23° C. for 1 hour. The coupling reaction was stopped by adding 5 µl of a 4M solution of hydroxylamine. Incubation was continued at 23° C. for an additional 0.25 hr. Dye-coupled nucleic acid was separated from unincorporated dye on an RNeasy® Mini kit or QIAquick PCR Purification Kit (QIAGEN Inc.—USA, Valencia, Calif). Samples were washed with 80% EtOH instead of buffer, as described above, and eluted twice with 50 µl volumes of 70° C. $H_2O$.

The spectrum of the labeled nucleic acid was measured from 220 nm–700 nm. The percent recovery of nucleic acid and molar incorporation of dye was calculated from extinction coefficients and absorbance values at $1_{max}$. Recovery of nucleic acid was typically ~80%. The mole percent of dye incorporated per nucleotide ranged from 1.5–5% of total nucleotides.

Yeast half-genome arrays were prepared essentially using the techniques described in U.S. patent application Ser. No. 09/303,082, filed Apr. 30, 1999. Briefly, PCR products containing common 5' and 3' sequences were obtained from Research Genetics (Huntsville, Ala.) and used as templates with amino-modified forward primers and unmodified reverse primers to amplify approximately one-half of the 6065 ORFs from the yeast genome. Amplification reactions that gave products of unexpected sizes were excluded from subsequent analysis. ORFs that could not be amplified from purchased templates were amplified from genomic DNA. DNA samples from 100 µl reactions were precipitated with isopropanol, resuspended in water, brought up to a total volume of 15 µl in 3×SSC, and transferred to 384-well microtiter plates. PCR products were robotically spotted onto 1×3 inch polylysine-coated glass slides. After printing, slides were processed as described by DeRisi et al. (Science 278: 680–86, 1997).

Half-genome arrays were then probed in duplicate with each of the cDNA pools prepared above. Microarrays were imaged on a prototype multi-frame charge-coupled device (CCD) camera (Applied Precision, Inc., Issaquah, Wash.). Each CCD image frame was approximately 2 mm square. Exposure times of 2 sec in the Cy5 channel (white light through a Chroma 618–648 nm excitation filter, Chroma 657–727 nm emission filter) and 1 sec in the Cy3 channel (Chroma 535–560 nm excitation filter, Chroma 570–620 nm emission filter) were taken consecutively in each frame before moving to the next, spatially contiguous frame. Color isolation between the Cy3 and Cy5 channels was 100:1 or better. Frames were knitted together in software to make the complete images. The intensity of each spot was quantified from the 10 µM pixels by frame-by-frame background subtraction and intensity averaging in each channel. Normalization between the channels was accomplished by normalizing each channel to the mean intensities of all genes. Alternatively, a commercial confocal laser scanner was used (General Laser Scanning, Watertown, Mass.).

Expression profiles were generated for each cycle number, in which the total fluorescence intensity of each individual open reading frame (ORF) was plotted versus the $\log_{10}$ of the ratio of red to green fluorescence (the expression ratio) for that ORF. Since the 3' cDNA pools were generated from the same yeast RNA preparation, any deviation from unity of the expression ratio for a given ORF indicates that a bias or infidelity has been introduced during the amplification process.

6.2. RESULTS AND DISCUSSION

The data from this experiment are shown in FIG. 2. When 25 cycles of PCR were performed (panel A), a large number of ORFs exhibited expression ratios that deviated from unity (and therefore $\log_{10}$ expression ratios that deviated from 0). The difference between the two 3' pools after 25 cycles of PCR was significant at p<0.1. Similar results are obtained at 20 and 15 cycles of PCR (panels B and C, respectively), although it is apparent that the deviation from unity is decreasing as the number of cycles of PCR decreases. When only 10 cycles of PCR were performed (panel D), there was essentially no deviation from unity for any ORF profiled, indicating that no bias was introduced.

In another experiment, PCR was performed as described by Zhao et al. (BioTechniques 24: 842–50, 1998). (The product of 35 cycles was re-amplified for another 35 cycles. Thus, a total of 70 cycles was used.) In this case, numerous ORFs showed expression ratios>100, indicating that significant biases were introduced. In our experience, therefore, the procedures of Zhao et al. (BioTechniques 24: 842–50, 1998) introduced sufficient biases during amplification such that the products are not suitable for gene expression analysis using DNA microarrays.

In this experiment, approximately 4×10$^6$ yeast cells, containing 10 µg of total cellular RNA or ~0.1 µg mRNA were used as starting material. In theory, after 10 cycles of PCR approximately 1024-($2^{10-}$) fold amplification of cDNA was produced. Given this degree of amplification, it would be necessary to start with at least 2×10$^5$ yeast cells in order to obtain the amounts of amplified DNA necessary for hybridization (1–5 µg per sample).

7. EXAMPLE 2

PCR-IVT Amplification of mRNA from Yeast

This example demonstrates that it is possible to do fewer cycles of PCR-IVT amplification than were used for PCR in Section 6 (Example 1), and amplify sufficient amounts of cRNA to maintain sufficient sensitivity to detect small changes in expression of the least abundant RNAs in the sample.

7.1. MATERIALS AND METHODS

Total RNA was amplified, using the 3'-end PCR/IVT method of the invention, from wt yeast and from a yeast strain having a homozygous deletion in the swi4 gene. Briefly, total RNA from each strain was reverse transcribed into ss cDNA using the RP#1 primer, then converted to ds cDNA using the Klenow enzyme and the FP#1 primer. The resultant ds cDNAs were then subjected to 10 cycles of amplification by PCR using the RP#3 primer and the FP#2 primer. The PCR-amplified cDNAs were then transcribed into RNA by reaction with T7 RNA polymerase for 16 hours at 37° C. The RNAP promoter introduced during the PCR step supports the transcription of antisense RNA from cDNA. RNAs were labeled during the IVT step by the inclusion of allylamine-derivatized UTP. Following IVT, unreacted NTPs were removed by using gel filtration or an RNeasy® Total RNA System kit (QIAGEN Inc.—USA, Valencia, Calif.). The cRNAs were labeled with the NHS esters of Cy3 and Cy5 ("Cy Dyes," Amersham Life Sciences, Pittsburgh, Pa.).

Yeast full-genome arrays were fabricated to contain essentially all the 6000 ORFs in wt yeast, essentially as described above. The arrays were probed in duplicate. One wt pool was labeled with Cy 3 and the other with Cy 5. Likewise, one swi4 pool was labeled with Cy 3 and the other with Cy 5. The arrays used the following pairwise combinations of amplified RNAs with one member of each pair labeled with Cy 3 and the other member labeled with Cy 5: wt pool #1 vs. wt pool #2, swi4 pool #1 vs. swi4 pool #2, wt pool #1 vs. swi4 pool #1, and wt pool #2 vs. swi4 pool #2. Imaging was performed as described in Section 6 (Example 1) above.

7.2. RESULTS AND DISCUSSION

Expression profiles were generated for each pairwise combination, in which the total fluorescence intensity of each individual open reading frame (ORF) was plotted versus the $\log_{10}$ of the ratio of red to green fluorescence (the expression ratio) for that ORF. Since the amplified RNAs were generated from the same yeast RNA preparation, it was expected that the $\log_{10}$(expression ratio) when wt pools were compared to each other, or when mutant pools were compared to each other would not deviate significantly from unity. If a deviation was seen, it would be indicative that the 3'-end PCR/IVT method of this invention results in biased amplification of transcripts. As can be seen from FIG. 3, panels A and B, there was no statistically significant deviation from unity at the p<0.01 level.

On the other hand, it was expected that the $\log_{10}$ (expression ratio) when wt was compared to mutant would deviate significantly from unity, reflecting the differences in gene expression between the two yeast strains. As can be seen from FIG. 3, panels C and D, this is the result that was observed. These results demonstrate that the 3'-end PCR/IVT amplification method of this invention preserves sequence and transcript representational fidelity, enabling real differences in gene expression to be detected with high sensitivity, but avoiding the introduction of bias artifacts that are common when high PCR cycle numbers are employed.

The last panel in FIG. 3, panel E, compares the signatures (ORFs for which the expression ratio was greater than or less than unity) obtained from panels C and D. If there was sequence or transcript representation bias introduced by the method of this invention, the signatures from panels C and D would not be expected to correlate. The data indicate that the correlation coefficient for these signatures is 0.98; hence, the results are highly correlated, indicating that no bias was introduced during amplification by the method of this invention.

In this experiment, approximately $4-8 \times 10^6$ yeast cells, containing 10 μg of total cellular RNA were used as starting material. After IVT, it is estimated that there is usually a 50-fold amplification relative to the amount of material present after PCR. Given this degree of amplification, it should be possible to start with as few as about $1 \times 10^6$ yeast cells and still maintain sufficient sensitivity to detect small changes in expression of the least abundant RNAs in the sample.

From 10 μg total cellular yeast RNA (or about 0.1 μg mRNA), we can obtain about 30–50 μg of cRNA after IVT. Thus, we can obtain about 300–500-fold amplification of the starting mRNA population.

With mammalian cells; we need about one-tenth the amount of starting total cellular RNA, i.e., about 1 μg (or about 0.01 μg mRNA), to obtain an equivalent amount of cRNA after IVT. With mammalian cells, we can obtain about 3,000–5,000-fold amplification.

8. EXAMPLE 3

Gene Regulation Profiles Detected with PCR-IVT Amplified Antisense RNA

This example demonstrates that the gene regulation profiles detected with antisense RNA amplified by the PCR/IVT method and with cDNA prepared by conventional reverse transcriptase methods are similar.

8.1. MATERIALS AND METHODS

Cultures of *S. cerevisiae* were treated with increasing concentrations of the immunosuppressive drug, FK506, as described by Marton et al. (Nature Med. 4: 1293–1301, 1998). Total cellular RNA was prepared from each culture and split into two aliquots. One aliquot was subjected to PCR/IVT amplification, and antisense RNA was derivatized with allylamine-UTP as described in Sections 6 and 7, and in FIGS. 1 and 3. From the second aliquot of total cellular RNA, polyA+ RNA was prepared and used as template for first strand cDNA synthesis. cDNA was labeled with Cy3 or Cy5 using the two step labeling procedure depicted in FIG. 1, except that allylamine-derivatized dUTP was incorporated during first strand cDNA synthesis. Following cDNA synthesis, unincorporated nucleotides were removed and allylamine-derivatized DNA molecules were labeled with N-hydroxysuccinimide esters of Cy3 or Cy5. Labeled RNA or DNA molecules from drug-treated cells were then mixed with labeled samples from untreated cells and these were then simultaneously hybridized to full genome *S. cerevisiae* DNA microarrays.

A set of 385 genes that were significantly up or down regulated (p<0.01) following treatment with FK506, as detected by either method, were then grouped according to their co-regulation behavior across this set of experiments (FIG. 4). Grouping was done using the 'hclust' hierarchical clustering algorithm as implemented in Matlab (MathWorks, Natick, Mass.). The distance metric for any gene pair is assigned typically to be 1–r, where r is the correlation coefficient of the regulation behavior of one gene compared with the other gene. The original up and down regulations for the chosen genes were then displayed in a color tabular format where green and red denote up and down regulation, respectively, and the gene order follows the order in the hierarchical clustering tree.

8.2. RESULTS AND DISCUSSION

Gene regulation profiles detected with antisense RNA amplified by the PCR/IVT method and with cDNA prepared by conventional reverse transcriptase methods were similar. The profiles in FIG. 4 show that the amplification procedure allows greater than about 2,000-fold amplification while introducing minimal biases.

9. EXAMPLE 4

PCR/IVT Permits Analysis of Drug Effects on Patient Lymphocyte Activation

This experiment was designed to measure the effects of immunosuppressive drugs on mRNA induction following activation of normal primary T cells from human blood. It demonstrates that PCR/IVT permits analysis of drug effects on patient lymphocyte activation. This type of analysis was not possible prior to the invention of the present invention because of limitations in the number of cells that can be obtained without harming a human donor. The use of primary lymphocytes is preferable to using cell lines because these cells mimic more closely the state of cells in a normal human.

9.1. MATERIALS AND METHODS

Mononuclear cells from ~60 ml of human peripheral blood were cultured for 5 days with the mitogenic lectin, phytohemagglutinin (PHA), and rested for one day in culture medium lacking PHA. Cells were then washed and individual cultures (1.5 ml containing $3 \times 10^6$ cells) were then incubated for 3 hrs with no drug (untreated), FK506 (10 ng/ml), or PP2 (tyrosine kinase inhibitor, Calbiochem, La Jolla, Calif., 12 mg/ml). Cells were then activated by adding them to 24 well plates coated with anti-CD3 monoclonal antibody (mAb, clone HIT3a, Pharmingen, San Diego, Calif.) and adding anti-CD28 mAb in solution (9.3 mAb, 1 mg/ml, gift of Dr. Jeff Ledbetter, Excite Therapies, Seattle, Wash.). At the indicated times, cultures were harvested and total cellular RNA was isolated using the TRIzol method (Life Technologies, Rockville, Md.). RNA was amplified by PCR/IVT, incorporating allylamine-UTP into the in vitro transcription step, and labeled using Cy3 and Cy5 NHS esters as described above in Sections 6–8. Labeled RNA pools representing unactivated cells amplified from ~1.5 ml of blood were mixed with RNA pools from the same number of cells activated minus or plus the indicated drugs, and hybridized to a DNA microarray comprising ~2,000 distinct human cDNAs. Identical samples were harvested at the indicated times following initiation of activation.

9.2. RESULTS AND DISCUSSION

FIG. 5 shows the $Log_{10}$ ratios of gene expression in activated cells versus unactivated cells for genes that were up or down regulated at a significance of p<0.1 by at least two-fold ($Log_{10} > 0.3$) in samples collected from at least two time points. Genes which were upregulated in activated cells have $Log_{10}$ red:green ratios greater than zero; genes down-regulated in activated cells have $Log_{10}$ red:green ratios less than zero. Fewer genes are displayed in the drug-treated samples because these drugs blocked gene expression of characteristic genes. Red and green are pseudo colors representing the fluorescent emissions of Cy5 and Cy3, respectively.

All references cited herein are incorporated herein by reference in their entirety and for all purposes to the same extent as if each individual publication, patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for amplifying at least one mRNA in a sample containing a plurality of different mRNAs comprising:

(a) synthesizing first strand cDNA by contacting under conditions conducive to reverse transcriptase activity at least one mRNA in said sample with (i) reverse transcriptase, and (ii) a first primer that is sufficiently complementary to a sequence in the mRNA so as to prime synthesis in a direction toward the 5' end of the mRNA;

(b) synthesizing double-stranded cDNA by contacting under conditions conducive to DNA polymerase activity the first strand cDNA with (i) a first DNA polymerase, and (ii) a second primer that is sufficiently complementary to a sequence 5' to said first primer sequence in said first strand cDNA so as to prime synthesis in a direction toward said first primer sequence; wherein neither said first primer nor said second primer comprises an RNA polymerase promoter sequence in sense or antisense orientation;

(c) amplifying the double-stranded cDNA by subjecting the double-stranded cDNA to a single round of polymerase chain reaction (hereinafter "PCR") of 20 cycles or less, wherein DNA is synthesized by use of a second DNA polymerase and a primer pair comprising a forward primer and a reverse primer, said forward primer and said reverse primer each being sufficiently complementary to a different strand of said double-stranded cDNA so as to prime synthesis in a template-dependent manner, wherein said forward primer or reverse primer comprises an RNA polymerase promoter sequence in sense or antisense orientation; and (d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced.

2. The method of claim 1 wherein in step (c) or less cycles of PCR are carried out.

3. The method of claim 1 wherein said first primer is a mixture of primers that prime synthesis in a direction toward the 5' end of substantially all the mRNAs in the sample and said second primer is a mixture of primers that prime synthesis of double-stranded cDNA from substantially all said first strand cDNAs produced in step (a).

4. The method of claim 2 wherein said first primer is a mixture of primers that prime synthesis in a direction toward the 5' end of substantially all the mRNAs in the sample and said second primer is a mixture of primers that prime synthesis of double-stranded cDNA from substantially all said first strand cDNAs produced in step (a).

5. The method of claim 3 wherein said first primer is a mixture of first primers, each primer comprising an oligo (dT) sequence and a 3' end sequence of 1–5 nucleotides, and said mixture of first primers comprising primers having an A, a G, or a C nucleotide present in each position of said 3' end sequence.

6. The method of claim 4 wherein said first primer is a mixture of first primers, each primer comprising an oligo (dT) sequence and a 3' end sequence of 1–5 nucleotides, and said mixture of first primers comprising primers having an A, a G, or a C nucleotide present in each position of said 3' end sequence.

7. The method of claim 5 wherein each primer in said mixture of first primers further comprises at its 5' end a selected sequence of 5–12 nucleotides.

8. The method of claim 6 wherein each primer in said mixture of first primers further comprises at its 5' end a selected sequence of 5–12 nucleotides.

9. The method of claim 3 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

10. The method of claim 4 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

11. The method of claim 7 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

12. The method of claim 8 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C or a T nucleotide present in each position of said 3' end sequence.

13. The method of claim 1 or 2 wherein said forward primer comprises said RNA polymerase promoter-sequence.

14. The method of claim 1 or 2 wherein said reverse primer comprises said RNA polymerase promoter sequence.

15. The method of claim 11 wherein said forward primer comprises a 3' end sequence of 8–12 nucleotides that is the same as the 5' end sequence of 8–12 nucleotides of the second primer, and said reverse primer comprises a 3' end sequence of 5–12 nucleotides that is the same as the 5' end sequence of 5–12 nucleotides of the first primer.

16. The method of claim 12 wherein said forward primer comprises a 3' end sequence of 8–12 nucleotides that is the same as the 5' end sequence of 8–12 nucleotides of the second primer, and said reverse primer comprises a 3' end sequence of 5–12 nucleotides that is the same as the 5' end sequence of 5–12 nucleotides of the first primer.

17. The method of claim 15 wherein said reverse primer comprises said RNA polymerase promoter sequence.

18. The method of claim 15 wherein said forward primer comprises said RNA polymerase promoter sequence.

19. The method of claim 1 wherein said sample contains total RNA or total mRNA from cells.

20. The method of claim 2, 3, 15 or 16 wherein said sample contains total RNA or total mRNA from cells.

21. The method of claim 19 wherein said cells are yeast cells.

22. The method of claim 19 wherein said cells are mammalian cells.

23. The method of claim 1 wherein said sample contains total RNA from $1 \times 10^6$ cells or less.

24. The method of claim 2 wherein said sample contains total RNA from $1 \times 10^6$ cells or less.

25. The method of claim 3, 15, 16, 17 or 18 wherein said sample contains total RNA from $1 \times 10^6$ cells or less.

26. The method of claim 1, wherein said first DNA polymerase is *E. coli* DNA polymerase I, Klenow fragment of *E. coli* DNA polymerase I, or T4 DNA polymerase.

27. The method of claim 1, wherein the RNA polymerase promoter sequence is a T7 RNA polymerase promoter sequence and the RNA polymerase is T7 RNA polymerase.

28. The method of claim 1, wherein the RNA polymerase promoter sequence is a T3 RNA polymerase promoter sequence and the RNA polymerase is T3 RNA polymerase.

29. The method of claim 1, wherein the RNA polymerase promoter sequence is an SP6 RNA polymerase promoter sequence and the RNA polymerase is SP6 RNA polymerase.

30. The method of claim 1, which further comprises labeling the transcribed cRNA with a label.

31. The method of claim 30, wherein the label is a fluorescent, radioactive, enzymatic, hapten, biotin, or digoxygenin label.

32. The method of claim 31, wherein the label is fluorescent.

33. The method of claim 32 wherein the fluorescent label is fluorescein isothiocyanate, lissamine, Cy3, Cy5, or rhodamine 110.

34. The method of claim 32, wherein a first aliquot of the cRNA is labeled with a first fluorophore having a first emission spectrum, and a second aliquot of the cRNA is labeled with a second fluorophore with a second emission spectrum differing from that of the first emission spectrum.

35. The method of claim 32, wherein the first fluorophore is Cy3 and the second fluorophore is Cy5.

36. The method of claim 1 or 2, further comprising, after the transcribing step, determining the presence or absence of a preselected target mRNA in said sample.

37. The method of claim 1, wherein the mRNA is derived from a population of cells.

38. The method of claim 37, wherein the population of cells is a eukaryotic population of cells.

39. The method of claim 38, wherein the eukaryotic population of cells is 106 or fewer mammalian cells.

40. The method of claim 1, wherein the first, second, forward, and reverse primers are each 24–48 nucleotides in length.

41. The method of claim 1, wherein the mRNA is extracted from at least one cell of interest, and further comprising contacting the cRNA produced in step (d) with an array containing one or more species of polynucleotide positioned at preselected sites on the array, under conditions conducive to hybridization; and detecting any hybridization that occurs between said one or more species of polynucleotide and said cRNA.

42. The method of claim 2, wherein the mRNA is extracted from at least one cell of interest, and further comprising contacting the cRNA produced in step (d) with an array containing one or more species of polynucleotide positioned at preselected sites on the array, under conditions conducive to hybridization; and detecting any hybridization that occurs between said one or more species of polynucleotide and said cRNA.

43. The method of claim 15, 16, 17 or 18, wherein the mRNA is extracted from at least one cell of interest, and further comprising contacting the cRNA produced in step (d) with an array containing one or more species of polynucleotide positioned at preselected sites on the array, under conditions conducive to hybridization; and detecting any hybridization that occurs between said one or more species of polynucleotide and said cRNA.

44. The method of claim 1 wherein said sample contains at least 10,000 different mRNAs.

45. A method for comparing the presence or amount of at least one mRNA of interest in a first sample and in a second sample, said first sample and said second sample each containing a plurality of different mRNAs from one or more cells, comprising:

(a) synthesizing first strand cDNA by contacting under conditions conducive to reverse transcriptase activity at least one mRNA in said first sample with (i) reverse transcriptase, and (ii) a first primer that is sufficiently complementary to a sequence in the mRNA so as to prime synthesis in a direction toward the 5' end of the mRNA;

(b) synthesizing double-stranded cDNA by contacting under conditions conducive to DNA polymerase activity the first strand cDNA with (i) a first DNA polymerase, and (ii) a second primer that is sufficiently complementary to a sequence 5' to said first primer sequence in said first strand cDNA so as to prime synthesis in a direction toward said first primer sequence; wherein neither said first primer nor said second primer comprises an RNA polymerase promoter sequence in sense or antisense orientation;

(c) amplifying the double-stranded cDNA by subjecting the double-stranded cDNA to a single round of PCR of 20 cycles or less, wherein DNA is synthesized by use of a second DNA polymerase and a primer pair comprising a forward primer and a reverse primer, said forward primer and said reverse primer each being sufficiently complementary to a different strand of said double-stranded cDNA so as to prime synthesis in a templatedependent manner, wherein said forward primer or reverse primer comprises an RNA polymerase promoter sequence in sense or antisense orientation;

(d) transcribing resultant amplified DNA into cRNA by contacting the amplified DNA with an RNA polymerase specific for said RNA polymerase promoter sequence introduced in step (c) under conditions conducive to RNA polymerase activity, such that cRNA is produced;

(e) labeling the cRNA produced in step (d) with a first label;

(f) repeating steps (a)–(d) with said second sample;

(g) labeling the cRNA produced in step (f) with a second label distinguishable from said first label;

(h) detecting or measuring the mRNA of interest in the first sample by contacting the cRNA labeled with said first label with a polynucleotide probe capable of hybridizing to said cRNA of the mRNA of interest under conditions conducive to hybridization; and detecting any hybridization that occurs between said probe and said cRNA;

(i) detecting or measuring the mRNA of interest in the second sample by contacting the cRNA labeled with said second label with said polynucleotide probe capable of hybridizing to said cRNA of the mRNA of interest under conditions conducive to hybridization; and detecting any hybridization that occurs between said probe and said cRNA; and (j) comparing the mRNA of interest detected or measured in said first sample with the mRNA of interest detected or measured in said second sample.

46. The method of claim 45 wherein in said amplifying steps 10 or less cycles of PCR are carried out.

47. The method of claim 45 wherein said first primer is a mixture of primers that prime synthesis toward the 5' end of substantially all the mRNAs in the sample and said second primer is a mixture of primers that prime synthesis of double-stranded cDNA from substantially all said first strand cDNAs produced in said steps of synthesizing first strand cDNA.

48. The method of claim 46 wherein said first primer is a mixture of primers that prime synthesis toward the 5' end of substantially all the mRNAs in the sample and said second primer is a mixture of primers that prime synthesis of double-stranded cDNA from substantially all said first strand cDNAs produced in said steps of synthesizing first strand cDNA.

49. The method of claim 47 wherein said first primer is a mixture of first primers, each primer comprising an oligo (dT) sequence and a 3' end sequence of 1–5 nucleotides, and said mixture of first primers comprising primers having an A, a G, or a C nucleotide present in each position of said 3' end sequence.

50. The method of claim 48 wherein said first primer is a mixture of first primers, each primer comprising an oligo (dT) sequence and a 3' end sequence of 1–5 nucleotides, and said mixture of first primers comprising primers having an A, a G, or a C nucleotide present in each position of said 3' end sequence.

51. The method of claim 49 wherein each primer in said mixture of first primers further comprise at its 5' end a selected sequence of 5–12 nucleotides.

52. The method of claim 50 wherein each primer in said mixture of first primers further comprises at its 5' end a selected sequence of 5–12 nucleotides.

53. The method of claim 47 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

54. The method of claim 48 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

55. The method of claim 51 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C, or a T nucleotide present in each position of said 3' end sequence.

56. The method of claim 52 wherein said second primer is a mixture of second primers, each primer comprising at its 5' end a selected sequence of 8–12 nucleotides, and at its 3' end a sequence of 1–6 nucleotides, said mixture of second primers comprising primers having an A, a G, a C or a T nucleotide present in each position of said 3' end sequence.

57. The method of claim 45 or 46 wherein said forward primer comprises said RNA polymerase promoter sequence.

58. The method of claim 45 or 46 wherein said reverse primer comprises said RNA polymerase promoter sequence.

59. The method of claim 55 wherein said forward primer comprises a 3' end sequence of 8–12 nucleotides that is the same as the 5' end sequence of 8–12 nucleotides of the second primer, and said reverse primer comprises a 3' end sequence of 5–12 nucleotides that is the same as the 5' end sequence of 5–12 nucleotides of the first primer.

60. The method of claim 56 wherein said forward primer comprises a 3' end sequence of 8–12 nucleotides that is the same as the 5' end sequence of 8–12 nucleotides of the second primer, and said reverse primer comprises a 3' end sequence of 5–14 nucleotides that is the same as the 5' end sequence of 5–12 nucleotides of the first primer.

61. The method of claim 55 wherein said reverse primer comprises said RNA polymerase promoter sequence.

62. The method of claim 59 wherein said reverse primer comprises said RNA polymerase promoter sequence.

63. The method of claim 45 wherein said sample contains total RNA or total mRNA from cells.

64. The method of claim 46 wherein said sample contains total RNA or total mRNA from cells.

65. The method of claim 59 or 60 wherein said sample contains total RNA or total mRNA from cells.

66. The method of claim 63 wherein said cells are yeast cells.

67. The method of claim 63 wherein said cells are mammalian cells.

68. The method of claim 45 wherein said sample contains total RNA from $1 \times 10^6$ cells or less.

69. The method of claim 46 wherein said sample contains total RNA from $1 \times 10^6$ cells or less.

70. The method of claim 59 or 60 wherein said sample contains total RNA from $1 \times 10^6$ cells or less.

71. The method of claim 45 wherein said first label is Cy3 and said second label is Cy5.

72. The method of claim 45 or 46 wherein said detecting or measuring steps (h) and (i) are carried out by a method comprising contacting said cRNA with an array containing one or more species of polynucleotide probe positioned at preselected sites on the array, under conditions conducive to hybridization; and detecting any hybridization that occurs between said polynucleotide probes and said cRNA.

73. The method of claim 63 or 68 wherein said detecting or measuring steps (h) and (i) are carried out by a method comprising contacting said cRNA with an array containing one or more species of polynucleotide probe positioned at preselected sites on the array, under conditions conducive to hybridization; and detecting any hybridization that occurs between said polynucleotide probes and said cRNA.

74. The method of claim 70 wherein said detecting or measuring steps (h) and (i) are carried out by a method comprising contacting said cRNA with an array containing one or more species of polynucleotide probe positioned at preselected sites on the array, under conditions conducive to hybridization; and detecting any hybridization that occurs between said polynucleotide probes and said cRNA.

75. The method of claim 41 wherein the array comprises a support with at least one surface and at least 100 different polynucleotide probes, each different polynucleotide probe comprising a different nucleotide sequence and being attached to the surface of the support in a different, selected location on said surface.

76. The method of claim 72 wherein the array comprises a support with at least one surface and at least 100 different polynucleotide probes, each different polynucleotide probe comprising a different nucleotide sequence and being attached to the surface of the support in a different, selected location on said surface.

77. The method of claim 41 wherein the nucleotide sequence of each of the different polynucleotide probes is in the range of 40–80 nucleotides in length.

78. The method of claim 41 wherein the polynucleotide probes comprise cDNA sequences.

79. The method of claim 41 wherein the array comprises polynucleotide probes of at least 2,000 different sequences.

80. The method of claim 41 wherein the nucleotide sequence of the polynucleotide probes are specific for at least 50% of the genes in the genome of the cells of interest.

81. The method of claim 41 wherein the polynucleotide probes hybridize to at least 10,000 different polynucleotide sequences.

82. The method of claim 41 wherein the array has at least 1,000 polynucleotide probes per 1 $cm^2$.

83. The method of claim 45 or 46 wherein in steps (h) and (i), the steps of contacting the cRNA labeled with said first label with said polynucleotide probe, and contacting the cRNA labeled with said second label with said polynucleotide probe, are carried out concurrently.

84. The method of claim 59 or 60 wherein in steps (h) and (i), the steps of contacting the cRNA labeled with said first label with said polynucleotide probe, and contacting the cRNA labeled with said second label with said polynucleotide probe, are carried out concurrently.

85. The method of claim 65 wherein in steps (h) and (i), the steps of contacting the cRNA labeled with said first label with said polynucleotide probe, and contacting the cRNA labeled with said second label with said polynucleotide probe, are carried out concurrently.

86. The method of claim 45 wherein said first sample contains mRNAs from cells that are diseased and wherein said second sample contains mRNAs from cells that are not so diseased.

87. A kit comprising in one or more containers:

(a) a mixture of first primers, each first primer comprising a 3' end sequence of 1–5 nucleotides, said mixture of first primers comprising primers having an A, a G, or a C nucleotide present in each position of said 3' end sequence; wherein each primer in said mixture of first primers further comprises at its 5' end an identical selected sequence of 5–12 nucleotides, and optionally further comprises an oligo (dT) sequence situated between said 5' end sequence and said 3' end sequence;

(b) a mixture of second primers, each second primer comprising at its 5' end an identical selected sequence of 8–12 nucleotides, and at its 3' end a sequence of 1–6 nucleotides, said mixture of second primers comprising primers having an A, a G, a C, or a T nucleotide present in each position of said 3' end sequence; wherein neither said first primer nor said second primer comprises an RNA polymerase promoter sequence in sense or antisense orientation; and (c) a primer pair suitable for use in PCR, said primer pair comprising a forward primer and a reverse primer, wherein said forward primer or reverse primer comprises an RNA polymerase promoter sequence in sense or antisense orientation.

88. The kit of claim 87 wherein the forward primer comprises said RNA polymerase promoter sequence.

89. The kit of claim 87 wherein said reverse primer comprises said RNA polymerase promoter sequence.

90. The kit of claim 87 wherein said forward primer comprises a 3' end sequence of 8– nucleotides that is the same as the 5' end sequence of 8–12 nucleotides of the second primer, and said reverse primer comprises a 3' end sequence of 5–12 nucleotides that is the same as the 5' end sequence of 5–12 nucleotides of the first primer.

91. The kit of claim 88 wherein said forward primer comprises a 3' end sequence of 8–12 nucleotides that is the same as the 5' end sequence of 8–12 nucleotides of the second primer, and said reverse primer comprises a 3' end sequence of 5–12 nucleotides that is the same as the 5' end sequence of 5-12 nucleotides of the first primer.

92. The kit of claim 87, which further comprises in a separate container an RNA polymerase specific to said RNA polymerase promoter.

93. The kit of claim 87 which further comprises a buffer for PCR.

94. The kit of claim 93 which further comprises a DNA polymerase.

95. The kit of claim 87, which further comprises:

(h) a set of directions for carrying out PCR; and (i) a set of directions for carrying out transcribing of amplified double-stranded cDNA into cRNA.

96. The kit of claim 87 further comprising a control nucleic acid.

97. The kit of claim 87 further comprising a microarray.

98. The kit of claim 97 further comprising means for stimulating and detecting fluorescent light emissions from fluorescently labeled RNA.

99. The kit of claim 98 further comprising expression profile projection and analysis software capable of being loaded into the memory of a computer system.

100. The method of claim 1 or 45 wherein said first primer comprises an oligo dT sequence.

101. The method of claim 1 or 45 wherein said first primer comprises a mixture of primers having an A, a G, a C, or a T nucleotide present in each position of the sequence of said primer.

102. The method of claim 1, 3, 4, 45, 48, or 49 wherein said second DNA polymerase of said amplifying step is thermostable.

* * * * *

UNITED STATES PATENT AND TRADEMARK OFFICE
CERTIFICATE OF CORRECTION

PATENT NO. : 6,271,002 B1
DATED : August 7, 2001
INVENTOR(S) : Linsley et al.

It is certified that error appears in the above-identified patent and that said Letters Patent is hereby corrected as shown below:

Column 39,
Line 56, please delete "step (c) or less cycles" and substitute therefor -- step (c) 10 or less cycles --.

Column 41,
Line 64, please delete "106 or fewer" and substitute therefor -- $10^6$ or fewer --.

Signed and Sealed this

Twenty-first Day of May, 2002

Attest:

JAMES E. ROGAN
Director of the United States Patent and Trademark Office

Attesting Officer

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 1
cctcctgcga agcttttttt tttttttv                                         28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
cctcctgcga agcttttttt ttttttt                                          27

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 3
taatacgact cactataggg aggacctcct gcgaagcttt tttttttttt t               51

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (25)..(28)
<223> OTHER INFORMATION: n=a, c, g or t

<400> SEQUENCE: 4
gttcgagacc tctagatgct gttgnnnn                                         28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
```

```
gttcgagacc tctagatgct gttg                                           24

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 6
taatacgact cactataggg aggagttcga gacctctaga tgctgttg                 48
```